(12) United States Patent
Van Himbergen et al.

(10) Patent No.: US 7,396,349 B2
(45) Date of Patent: Jul. 8, 2008

(54) WRAPPED ABSORBENT CORE

(75) Inventors: James George Van Himbergen, Kimberly, WI (US); Mark Scott Lancaster, Neenah, WI (US); Michael Barth Venturino, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/955,769

(22) Filed: Sep. 30, 2004

(65) Prior Publication Data
US 2006/0069368 A1 Mar. 30, 2006

(51) Int. Cl.
*A61F 13/15* (2006.01)
(52) U.S. Cl. ............... 604/385.101; 604/378; 604/385.14; 604/376; 604/385.01
(58) Field of Classification Search ........ 604/378, 604/385.14, 385.101, 376; 156/216, 213
See application file for complete search history.

(56) References Cited

U.S. PATENT DOCUMENTS

| | | | |
|---|---|---|---|
| 3,338,992 | A | 8/1967 | Kinney |
| 3,341,394 | A | 9/1967 | Kinney |
| 3,502,763 | A | 3/1970 | Hartmann |
| 3,509,881 | A * | 5/1970 | Sabee ............ 604/397 |
| 3,542,615 | A | 11/1970 | Dobo et al. |
| 3,692,618 | A | 9/1972 | Dorschner et al. |
| 3,730,798 | A | 5/1973 | Franz |
| 3,802,817 | A | 4/1974 | Matsuki et al. |
| 3,844,288 | A * | 10/1974 | Kiela ............ 604/379 |
| 3,849,241 | A | 11/1974 | Butin et al. |
| 3,913,579 | A * | 10/1975 | Srinivasan et al. .......... 604/366 |
| 4,041,203 | A | 8/1977 | Brock et al. |
| 4,100,324 | A | 7/1978 | Anderson et al. |
| 4,324,247 | A * | 4/1982 | Aziz ............ 604/371 |
| 4,340,563 | A | 7/1982 | Appel et al. |
| 4,372,312 | A | 2/1983 | Fendler et al. |
| 4,610,685 | A * | 9/1986 | Raley ............ 604/366 |

(Continued)

FOREIGN PATENT DOCUMENTS

EP 0 217 032 B1 2/1992

(Continued)

OTHER PUBLICATIONS

International Search Report for PCT/US2005/020932, dated Nov. 3, 2005, 3 pages.

(Continued)

*Primary Examiner*—Jacqueline Stephens
(74) *Attorney, Agent, or Firm*—Armstrong Teasdale, LLP

(57) ABSTRACT

In an absorbent structure for an absorbent article, a non-woven absorbent core extends from one longitudinal end region of the absorbent structure through a central region thereof to an opposite longitudinal end region of the absorbent structure. The absorbent core has a first face, a second face opposite the first face, and laterally opposite side edges. A liquid permeable wrapsheet is wrapped about the first face, the laterally opposite side edges and at least a portion of the second face of the absorbent core to define a wrapped configuration of the wrapsheet. The wrapsheet is constructed of a non-woven material and is secured in its wrapped configuration about the absorbent core at at least one securement region having a length substantially less than the length of the absorbent structure.

21 Claims, 31 Drawing Sheets

U.S. PATENT DOCUMENTS

| | | | |
|---|---|---|---|
| 4,663,220 A | 5/1987 | Wisneski et al. | |
| 4,699,621 A * | 10/1987 | Stevens et al. | 604/385.29 |
| 4,704,116 A | 11/1987 | Enloe et al. | |
| 4,798,603 A | 1/1989 | Meyer et al. | |
| 4,819,928 A | 4/1989 | Osborn et al. | |
| 5,176,668 A | 1/1993 | Bernardin | |
| 5,176,672 A | 1/1993 | Bruemmer et al. | |
| 5,192,606 A | 3/1993 | Proxmire et al. | |
| 5,213,881 A | 5/1993 | Timmons et al. | |
| 5,226,992 A | 7/1993 | Morman | |
| 5,284,703 A | 2/1994 | Everhart et al. | |
| 5,350,624 A | 9/1994 | Georger et al. | |
| 5,458,592 A | 10/1995 | Abuto et al. | |
| 5,486,166 A | 1/1996 | Bishop et al. | |
| 5,490,846 A | 2/1996 | Ellis et al. | |
| 5,496,298 A | 3/1996 | Kuepper et al. | |
| 5,509,915 A | 4/1996 | Hanson et al. | |
| 5,540,796 A | 7/1996 | Fries | |
| 5,582,603 A | 12/1996 | Difilippantonio et al. | |
| 5,595,618 A | 1/1997 | Fries et al. | |
| 5,607,798 A * | 3/1997 | Kobylivker et al. | 442/381 |
| 5,611,879 A * | 3/1997 | Morman | 156/201 |
| 5,695,324 A * | 12/1997 | Weirich | 604/378 |
| 5,769,834 A * | 6/1998 | Reiter et al. | 604/385.12 |
| 5,827,258 A * | 10/1998 | McFall et al. | 604/385.01 |
| 5,855,719 A | 1/1999 | Menard | |
| 5,944,704 A * | 8/1999 | Guarracino et al. | 604/359 |
| 5,954,705 A * | 9/1999 | Sawaki et al. | 604/385.101 |
| 5,993,433 A | 11/1999 | St. Louis et al. | |
| 6,210,309 B1 | 4/2001 | Smithe et al. | |
| 6,214,274 B1 | 4/2001 | Melius et al. | |
| 6,248,097 B1 | 6/2001 | Beitz et al. | |
| 7,008,363 B2 | 3/2006 | Allen et al. | |
| 2001/0037102 A1 * | 11/2001 | Sugito | 604/385.13 |
| 2003/0078557 A1 * | 4/2003 | Vergona | 604/385.28 |
| 2003/0113507 A1 | 6/2003 | Niemeyer et al. | |
| 2003/0144641 A1 * | 7/2003 | Chen et al. | 604/368 |
| 2003/0158531 A1 * | 8/2003 | Chmielewski | 604/366 |

FOREIGN PATENT DOCUMENTS

| | | |
|---|---|---|
| EP | 0 951 886 A1 | 10/1999 |
| EP | 980681 A1 | 2/2000 |
| WO | WO 97/07761 A1 | 3/1997 |
| WO | WO 01/60731 A2 | 8/2001 |

OTHER PUBLICATIONS

International Search Report for PCT/US2005/020933, dated Sep. 15, 2006, 3 pages.

* cited by examiner

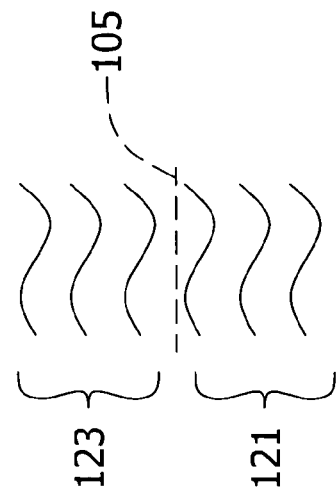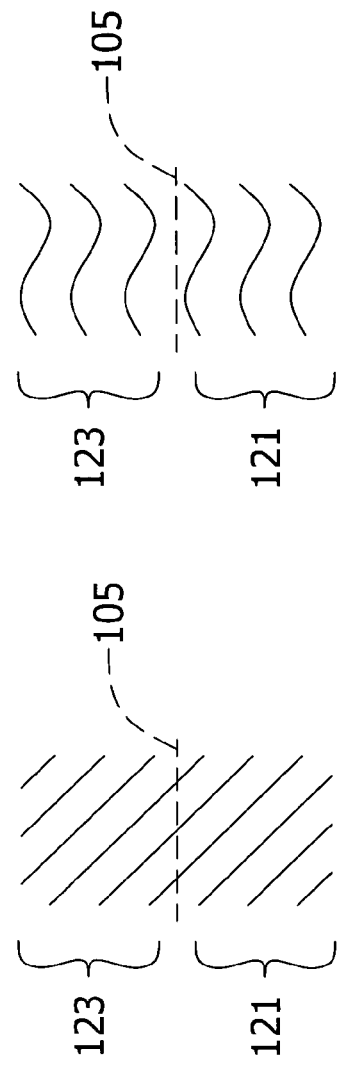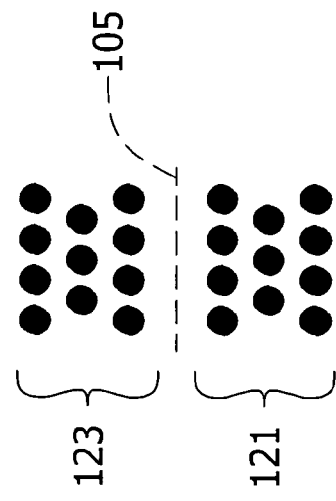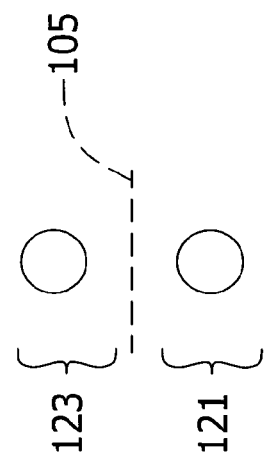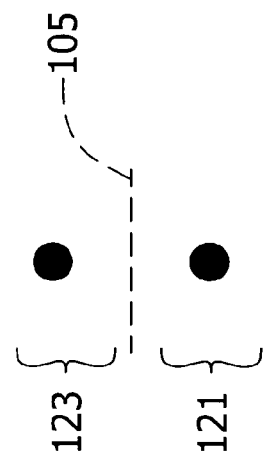

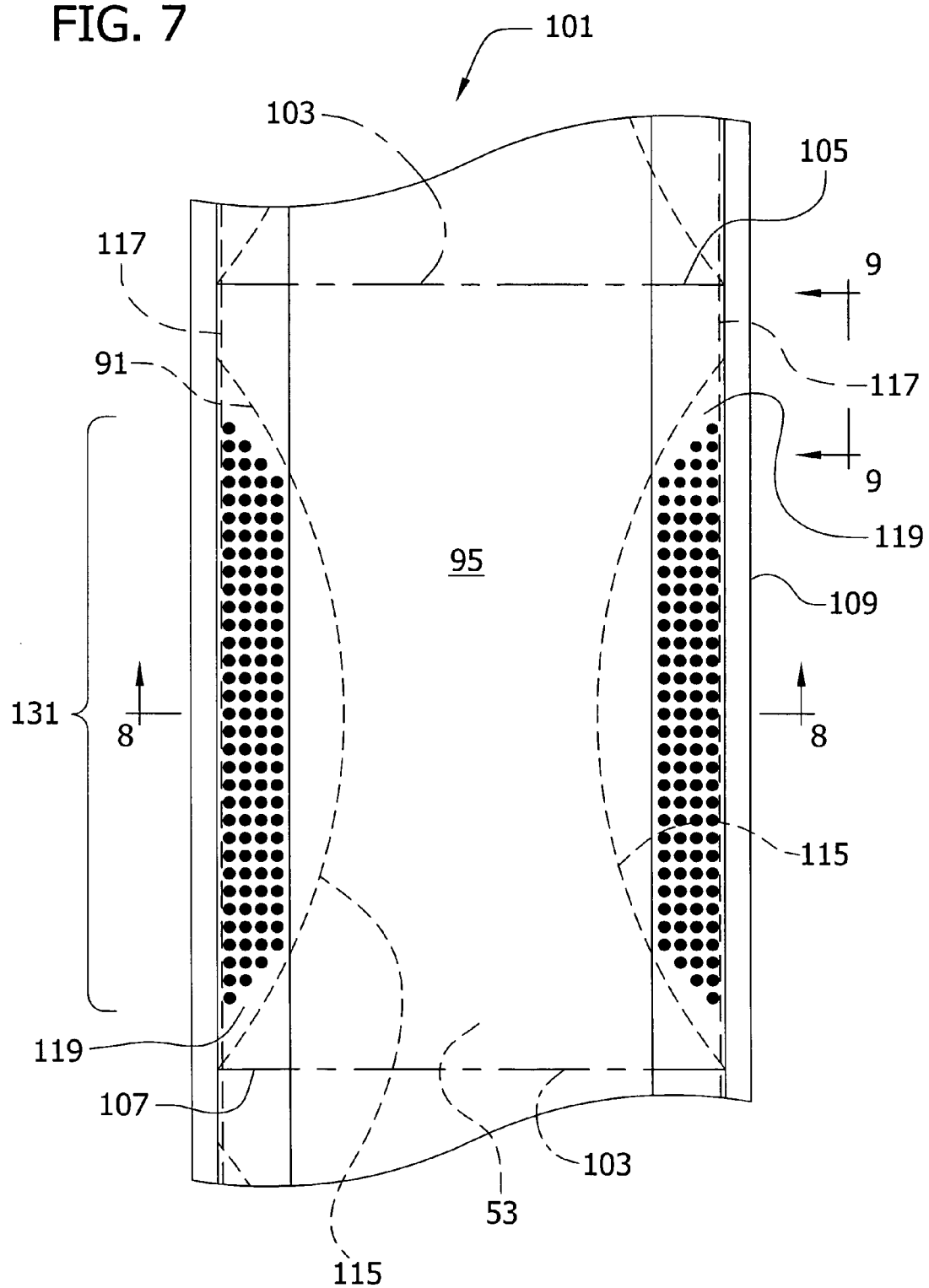

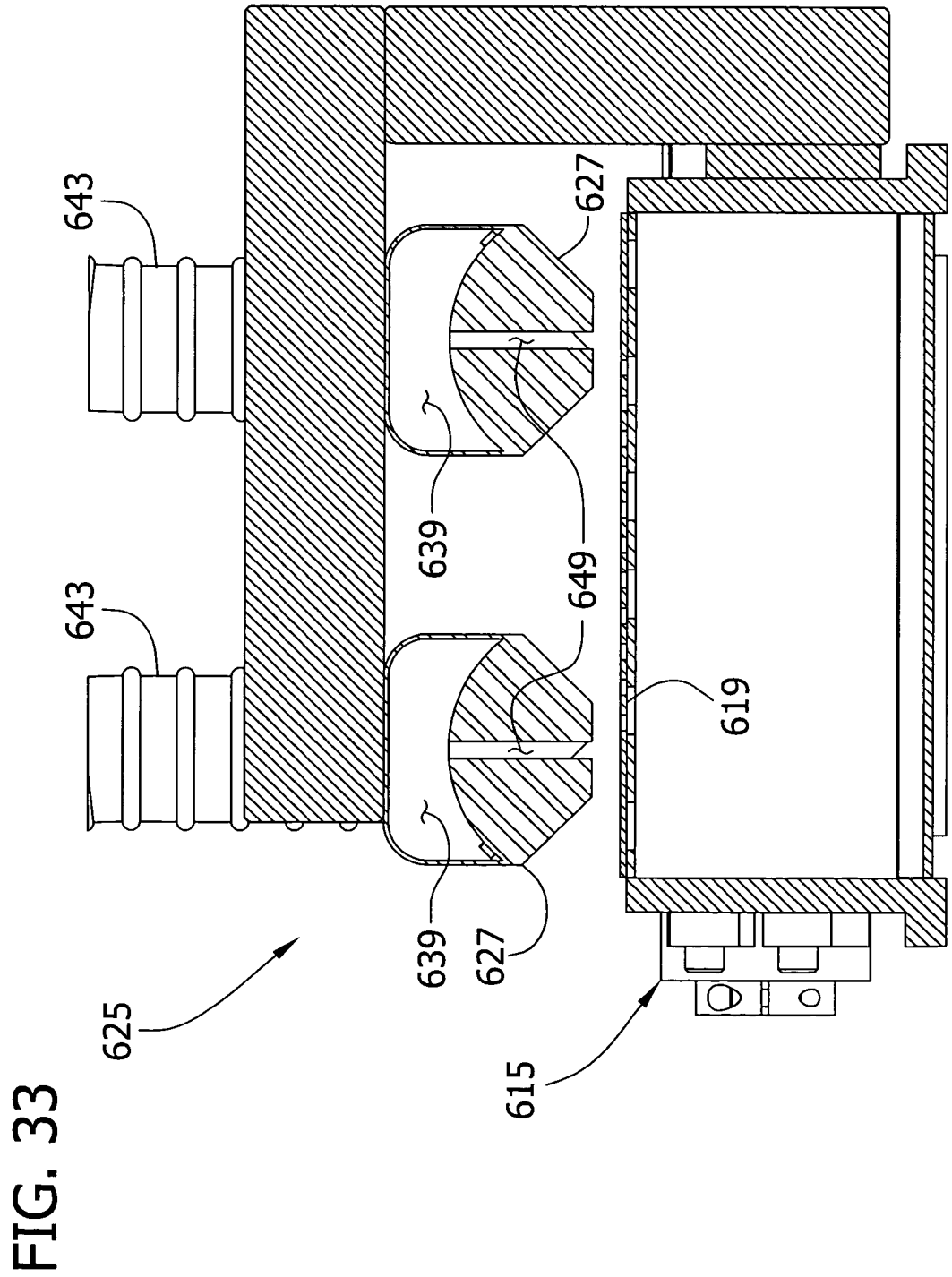

WRAPPED ABSORBENT CORE

BACKGROUND OF THE INVENTION

The present invention relates generally to absorbent articles intended for personal wear, more particularly to an absorbent structure for a personal wear absorbent article used to take-in and retain body exudates released by a wearer of the article, and even more particularly to such an absorbent article in which the absorbent structure comprises an absorbent core that is wrapped by a liquid permeable wrapsheet to maintain the integrity of the absorbent core when wet and to inhibit migration of absorbent core materials.

Absorbent articles for personal wear are in widespread use, such as diapers, children's toilet training pants, adult incontinence garments, sanitary napkins and the like, as well as surgical bandages and sponges, to take-in and retain body exudates released by a wearer. Certain absorbent articles are generally considered to be disposable in that they are usually intended to be discarded after a limited period of use, i.e., the articles are not intended to be laundered or otherwise restored for reuse. Disposable absorbent articles typically comprise an absorbent structure disposed between a liner, which contacts the wearer's skin, and an outer cover, which inhibits liquid body waste absorbed by the absorbent structure from leaking out of the article.

The liner of the absorbent article is typically liquid permeable to permit liquid body waste to pass therethrough for absorption by the absorbent body. Absorbent articles such as diapers, training pants, incontinence garments and other articles intended to take-in and retain large amounts of liquid body waste (e.g., urine) typically require the use of high absorbency, superabsorbent materials to provide the needed absorbent capacity. More particularly, superabsorbent particles or fibers are blended with woodpulp or synthetic fibers to form an absorbent core (also sometimes referred to as an absorbent body).

While conventional absorbent articles perform well functionally, it is becoming more desirable that such absorbent articles appear more like conventional garments. For example, diapers, children's toilet training pants and incontinence garments desirably appear more similar to conventional cloth underpants. To accomplish this, absorbent articles must be thinner, softer and more conformable to the wearer's body than currently available products. One feature that would facilitate a thinner and more comformable appearance is a thinner absorbent structure. Specifically, the ratio of superabsorbent material to fiber within the absorbent core may be substantially increased to maintain and/or increase the absorbent capacity of the absorbent structure while reducing the amount of fluff (e.g., fibers) needed.

Such absorbent cores, however, are often unable to adequately contain the superabsorbent particles therein. As a result, dry superabsorbent particles can escape from the article prior to use, and wet particles can migrate from the absorbent core to the skin of the wearer (otherwise referred to as gel-on-skin occurrence in reference to the hydrogel construction of the superabsorbent material). Although superabsorbent gel particles have not been observed to adversely affect skin health, the occurrence of foreign particles on the skin of an infant is not preferred by consumers and thus is not desirable.

It is also known to provide a tissue wrapsheet surrounding the absorbent core to maintain the structural integrity of the core prior to wetting of the article. However, providing a tissue wrapsheet surrounding the absorbent core is not likely to alleviate such a concern because the tissue wrapsheet loses its integrity once it becomes wet and results in superabsorbent material readily migrating through the wrapsheet.

SUMMARY OF THE INVENTION

In general, an absorbent structure according to one embodiment of the present invention has longitudinal end regions and a central region extending longitudinally between and interconnecting the longitudinal end regions. The absorbent structure generally comprises a non-woven absorbent core extending from one longitudinal end region of the absorbent structure through the central region thereof to the opposite longitudinal end region of the absorbent structure. The absorbent core has a first face, a second face opposite the first face, and laterally opposite side edges. A liquid permeable wrapsheet is wrapped about the first face, the laterally opposite side edges and at least a portion of the second face of the absorbent core to define a wrapped configuration of the wrapsheet. The wrapsheet is constructed at least in part of a non-woven material and is secured in its wrapped configuration about the absorbent core at at least one securement region having a length substantially less than the length of the absorbent structure.

In another embodiment, the absorbent structure generally comprises a non-woven absorbent core extending from one longitudinal end region of the absorbent structure through the central region thereof to the opposite longitudinal end region of the absorbent structure. The absorbent core has a first face, a second face opposite the first face, and laterally opposite side edges. A cover layer covers at least a portion of the second face of the absorbent core. A liquid permeable wrapsheet is wrapped about the first face, the laterally opposite side edges and at least a portion of the cover layer covering the second face of the absorbent core to define a wrapped configuration of the wrapsheet. The wrapsheet is constructed at least in part of a non-woven material and is secured in its wrapped configuration about the absorbent core at at least one securement region having a length substantially less than the length of the absorbent structure.

A continuous absorbent structure web according to an embodiment of the present invention generally comprises a non-woven absorbent core material having a first face, a second face opposite the first face, and laterally opposite side edges. A continuous liquid permeable wrapsheet web is wrapped about the first face, the laterally opposite side edges and at least a portion of the second face of the absorbent core material to define a wrapped configuration of the wrapsheet web. The wrapsheet web is constructed at least in part of a non-woven material and is secured in its wrapped configuration about the absorbent core material at least at two securement regions for each absorbent structure to be subsequently cut from the absorbent structure web. The at least two securement regions are spaced longitudinally from each other and disposed at longitudinal end regions of the absorbent structure to be cut from the absorbent structure web. The securement region at one end region of an absorbent structure of the web is formed integrally with the securement region at the end region of an adjacent absorbent structure of the web.

Other features of the invention will be in part apparent and in part pointed out hereinafter.

BRIEF DESCRIPTION OF THE DRAWINGS

FIGS. 6a, 6b, 6c, 6d, and 6e illustrate different bonding patterns for securing a wrapsheet in a wrapped configuration about an absorbent core;

FIG. 7 is a fragmented plan view of a second embodiment of a continuous absorbent structure web of the present invention;

FIG. 33 is a partial cross-section taken in the plane of line 33-33 of FIG. 30.

Corresponding reference characters indicate corresponding parts throughout the several views of the drawings.

DETAILED DESCRIPTION OF THE INVENTION

Figure 1:
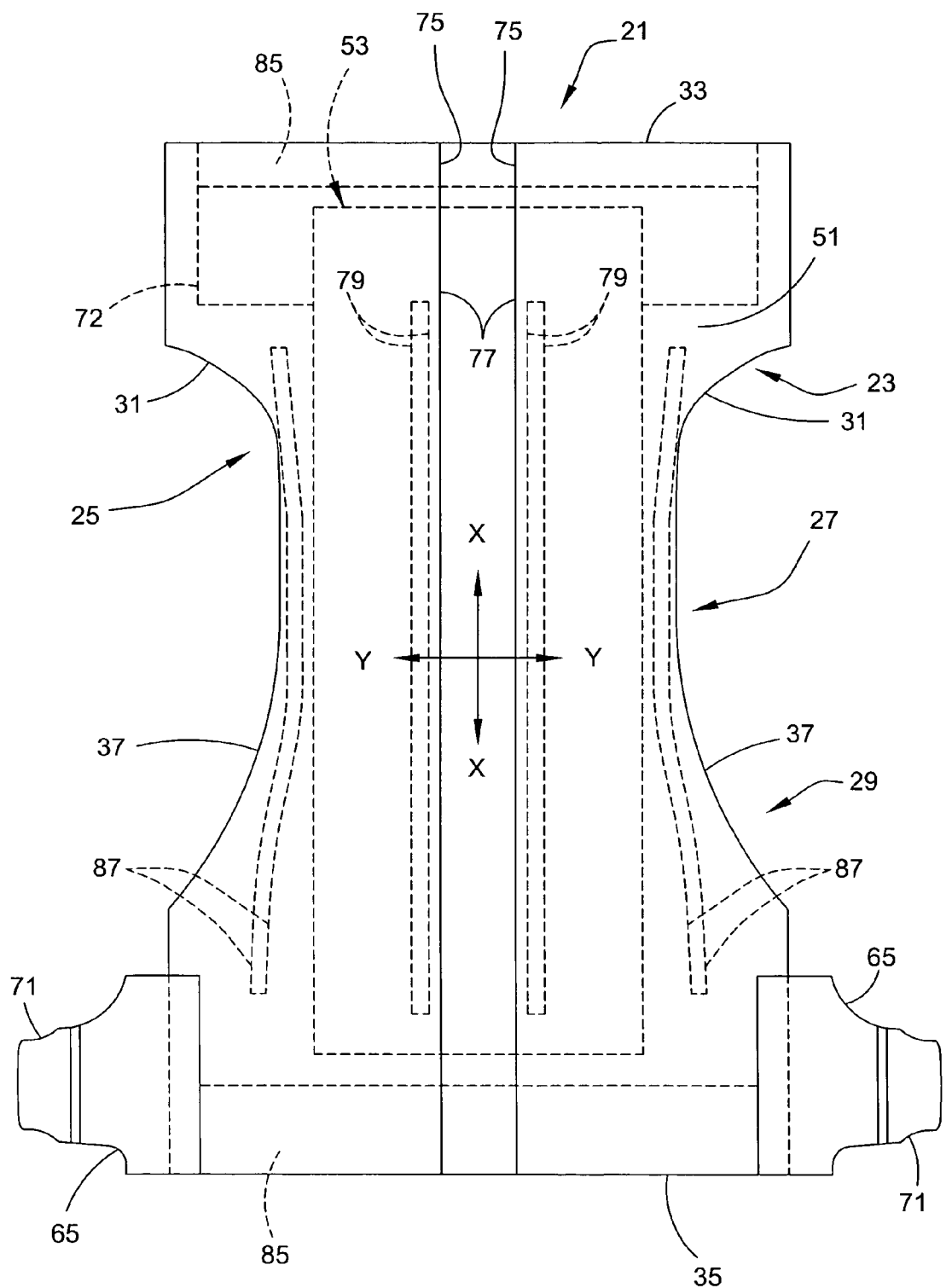
FIG. 1 is plan view of an absorbent article of the present invention illustrated in the form of a diaper shown unfastened and laid flat, with the surface that faces a wearer facing up and internal components shown in hidden lines.
Figure 2:
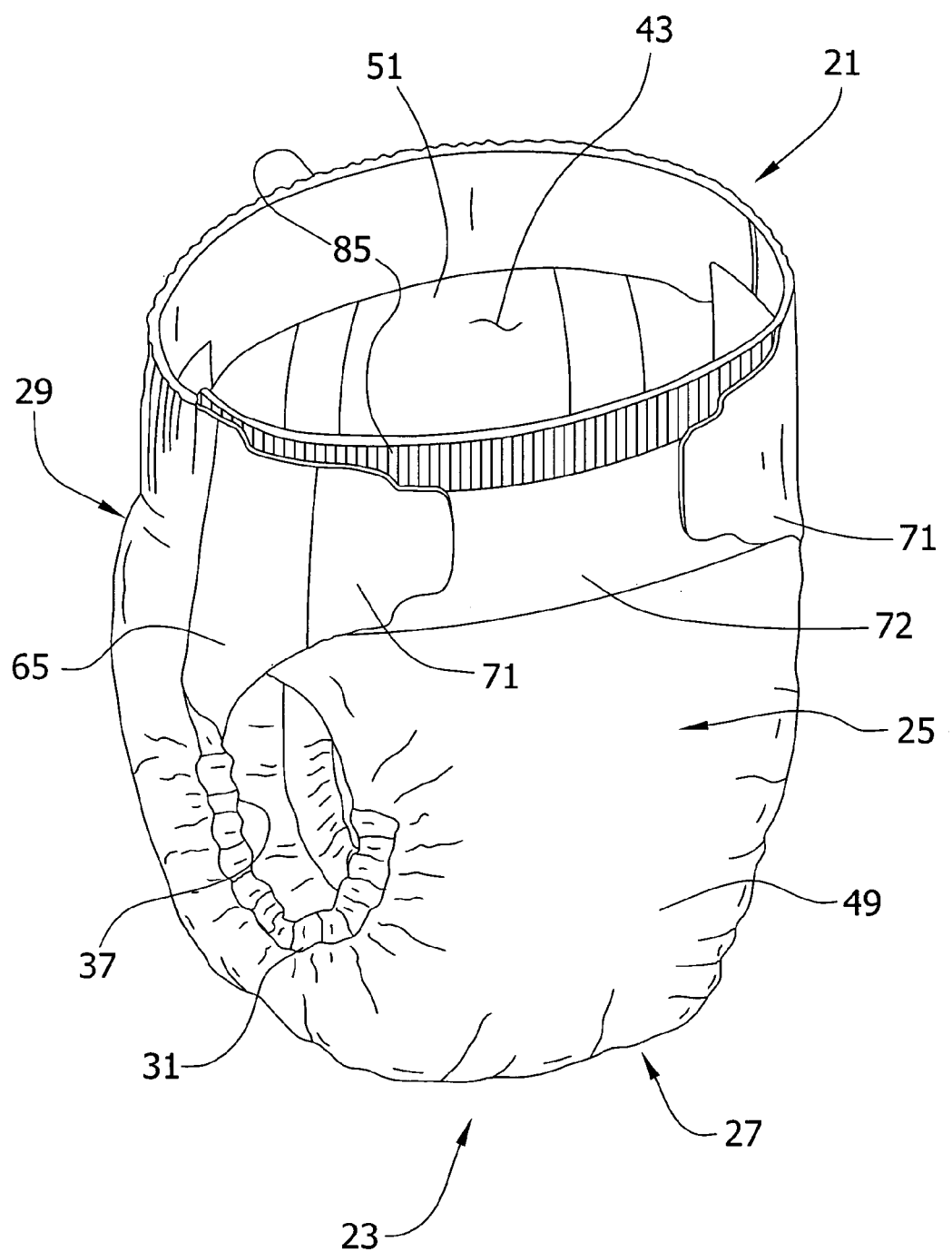
FIG. 2 is a perspective view of the diaper shown as worn.

Referring now to the drawings and in particular to FIGS. 1 and 2, one embodiment of an absorbent article incorporating a wrapped absorbent core of the present invention is representatively illustrated therein in the form of a diaper, which is indicated in its entirety by the reference numeral 21. As used herein, an absorbent article refers to an article which may be placed against or in proximity to the body of the wearer (e.g., contiguous to the body) to absorb and/or retain various waste discharged from the body. Some absorbent articles, such as disposable absorbent articles, are intended to be discarded after a limited period of use instead of being laundered or otherwise restored for reuse. It is contemplated, however, that the principles of the present invention have application in garments (including reusable garments) and other absorbent articles. For example, the principles of the present invention may be incorporated into children's training pants and other infant and child care products, adult incontinence garments and other adult care products, medical garments, sanitary napkins and other feminine care products and the like, as well as surgical bandages and sponges.

The diaper 21 is shown in FIG. 1 in an unfolded and laid-flat condition to illustrate a longitudinal axis X and a lateral axis Y of the diaper. The diaper 21 generally comprises a central absorbent assembly 23 extending longitudinally from a front (e.g., anterior) region 25 of the diaper through a crotch (e.g., central) region 27 to a back (e.g., posterior) region 29 of the diaper. The front region 25 generally includes the portions of the central absorbent assembly 23 which extend over the wearer's lower abdominal region and the back region 29 generally includes the portions of the central absorbent assembly which extend over the wearer's lower back region. The crotch region 27 includes the portion extending longitudinally through the wearer's crotch from the front region 25 to the back region 29 and laterally between the wearer's legs.

The central absorbent assembly 23 is generally I-shaped, and more particularly hourglass shaped, and has contoured, laterally opposite side edges 31 and longitudinally opposite front and rear waist edges or ends, respectively designated 33 and 35. It is understood, however, that the diaper 21 may have other shapes, such as a rectangular shape or a T-shape without departing from the scope of the present invention. The side edges 31 of the diaper 21 extend longitudinally from the front region 25 through the crotch region 27 to the back region 29 for forming transversely spaced leg openings 37 (FIG. 2) of the diaper when worn. As worn on the wearer's body (FIG. 2), the diaper 21 further defines a central waist opening 43 and the leg openings 37.

The central absorbent assembly 23 of the diaper 21 comprises an outer cover, generally indicated at 49 in FIG. 1, a bodyside liner 51 (FIG. 1) positioned in opposed relation with the outer cover, and an absorbent structure, generally indicated at 53 in FIG. 1, of the present invention disposed between the outer cover and the liner. The outer cover 49 of the illustrated embodiment generally defines the length and width of the diaper 21. The absorbent structure 53 has a length and width which are each less than the respective length and width of the outer cover 49 such that the outer cover extends both longitudinally and laterally out beyond the sides and ends of the absorbent structure. The bodyside liner 51 may be generally coextensive with the outer cover 49, or may instead overlie an area which is larger (and would thus generally define the length and/or width of the diaper 21) or smaller than the area of the outer cover 49, as desired. In other words, the bodyside liner 51 is in superposed relationship with the outer cover 49 but may not necessarily be coextensive with the outer cover.

In one embodiment, the outer cover 49 is stretchable and may or may not be somewhat elastic. More suitably, the outer cover 49 is sufficiently extensible such that once stretched under the weight of the insulted absorbent structure, the outer cover will not retract substantially back toward its original position. However, it is contemplated that the outer cover 49 may instead be generally non-extensible and remain within the scope of this invention.

The outer cover 49 may be a multi-layered laminate structure to provide desired levels of extensibility as well as liquid impermeability and vapor permeability. For example, the outer cover 49 of the illustrated embodiment is of two-layer construction, including an outer layer constructed of a vapor permeable material and an inner layer constructed of a liquid impermeable material, with the two layers being secured together by a suitable laminate adhesive. It is understood, however, that the outer cover 49 may instead be constructed of a single layer of liquid impermeable material, such as a thin plastic film, without departing from the scope of this invention. The liquid impermeable inner layer of the outer cover 49 can be either vapor permeable (i.e., "breathable") or vapor impermeable.

The bodyside liner 51 is suitably pliable, soft feeling, and nonirritating to the wearer's skin, and is employed to help isolate the wearer's skin from the absorbent structure 53. The liner 51 is less hydrophilic than the absorbent structure 53 to present a relatively dry surface to the wearer, and is sufficiently porous to be liquid permeable to thereby permit liquid to readily penetrate through its thickness. A suitable bodyside liner 51 may be manufactured from a wide selection of web materials, but is suitably capable of stretching in at least one direction (e.g., longitudinal or lateral). In particular embodiments, the bodyside liner 51 is extensible and capable of extending along with the outer cover 49 for desired fit of the diaper 21 on the wearer.

Fastener tabs 65 are secured to the central absorbent assembly 23 generally at the back region 29 thereof with the tabs extending laterally out from the opposite side edges 31 of the assembly. The fastener tabs 65 may be attached to the outer cover 49, to the bodyside liner 51, between the outer cover and liner, or to other components of the diaper 21. The tabs 65 may also be elastic or otherwise rendered elastomeric. For example, the fastener tabs 65 may be an elastomeric material such as a neck-bonded laminate (NBL) or stretch-bonded laminate (SBL) material.

Methods of making such materials are well known to those skilled in the art and are described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987 in the names of Taylor et al., the disclosures of which are hereby incorporated by reference. Examples of articles that include selectively configured fastener tabs are described in U.S. Pat. No. 5,496,298 issued Mar. 5, 1996 to Kuepper et al.; U.S. Pat. No. 5,540,796 to Fries; and U.S. Pat. No. 5,595,618 to Fries; the disclosures of which are also incorporated herein by reference. Alternatively, the fastener tabs 65 may be formed integrally with a selected diaper component. For example, the tabs may be formed integrally with the inner or outer layer of the outer cover, or with the bodyside liner.

Fastening components, such as hook and loop fasteners, designated 71 and 72 respectively, are employed to secure the diaper 21 on the body of a child or other wearer. Alternatively, other fastening components (not shown), such as buttons, pins, snaps, adhesive tape fasteners, cohesives, mushroom-and-loop fasteners, or the like, may be employed. Desirably, the interconnection of the fastening components 71, 72 is selectively releasable and re-attachable. In the illustrated embodiment, the hook fasteners 71 are secured to and extend laterally out from the respective fastener tabs 65 at the back region 29 of the diaper 21. However, it is understood that the fastener tabs 65 may be formed of a hook material and thus comprise the hook fasteners 71 without departing from the scope of this invention. The loop fastener 72 of the illustrated embodiment is a panel of loop material secured to the outer cover 49 at the front region 25 of the diaper 21 to provide a "fasten anywhere" mechanical fastening system for improved fastening of the hook fasteners 71 with the loop fastener.

The diaper 21 shown in FIG. 1 also comprises a pair of containment flaps 75 configured to provide a barrier to the lateral flow of body exudates. The containment flaps 75 are located generally adjacent laterally opposite side edges 31 of the diaper 21 and, when the diaper is laid flat as shown in FIG. 1, extend inward toward the longitudinal axis X of the diaper. Each containment flap 75 typically has a free, or unattached end 77 free from connection with the bodyside liner 51 and other components of the diaper 21. Elastic strands 79 disposed within the flaps 75 adjacent the unattached ends thereof urge the flaps toward an upright, perpendicular configuration in at least the crotch region 27 of the diaper 21 to form a seal against the wearer's body when the diaper is worn. The containment flaps 75 may extend longitudinally the entire length of the diaper 21 or they may extend only partially along the length of the diaper. When the containment flaps 75 are shorter in length than the diaper 21, the flaps can be selectively positioned anywhere between the side edges 31 of the diaper 21 in the crotch region 27. In a particular aspect of the invention, the containment flaps 75 extend the entire length of the diaper 21 to better contain the body exudates.

Such containment flaps 75 are generally well known to those skilled in the art and therefore will not be further described herein except to the extent necessary to describe the present invention. As an example, suitable constructions and arrangements for containment flaps 75 are described in U.S. Pat. No. 4,704,116 issued Nov. 3, 1987, to K. Enloe, the disclosure of which is hereby incorporated by reference. The diaper 21 may also incorporate other containment components in addition to or instead of the containment flaps 75. For example, while not shown in the drawings, other suitable containment components may include, but are not limited to, elasticized waist flaps, foam dams in the front, back and/or crotch regions, and the like.

The diaper 21 can also include a surge management layer (not shown) which helps to decelerate and diffuse surges or gushes of liquid that may be rapidly introduced into the absorbent body 53. Desirably, the surge management layer can rapidly accept and temporarily hold the liquid prior to releasing the liquid to the absorbent structure. In the illustrated embodiment, for example, a surge layer can be located between the absorbent body 53 and the bodyside liner 51. Examples of suitable surge management layers are described in U.S. Pat. No. 5,486,166 entitled FIBROUS NON-WOVEN WEB SURGE LAYER FOR PERSONAL CARE ABSORBENT ARTICLES AND THE LIKE by C. Ellis and D. Bishop, which issued Jan. 23, 1996, and U.S. Pat. No. 5,490,846 entitled IMPROVED SURGE MANAGEMENT FIBROUS NON-WOVEN WEB FOR PERSONAL CARE ABSORBENT ARTICLES AND THE LIKE by C. Ellis and R. Everett, which issued Feb. 13, 1996, the entire disclosures of which are hereby incorporated by reference in a manner that is consistent herewith.

To provide improved fit and to help further reduce leakage of body exudates from the diaper 21, elastic components are typically incorporated therein, particularly at the waist area and the leg areas. For example, the diaper 21 of the illustrated embodiment of FIGS. 1 and 2 has waist elastic components 85 and leg elastic components 87. The waist elastic components 85 are configured to gather and shirr the end margins of the diaper 21 to provide a resilient, comfortable close fit around the waist of the wearer and the leg elastic components 87 are configured to gather and shirr the side margins of the diaper at the leg openings 37 to provide a close fit around the wearer's legs.

Examples of other suitable diaper 21 configurations are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., U.S. Pat. No. 5,509,915 issued Apr. 23, 1996 to Hanson et al., U.S. Pat. No. 5,993,433 issued Nov. 30, 1999 to St. Louis et al., and U.S. Pat. No. 6,248,097 issued Jun. 19, 2001 to Beitz et al., the disclosures of which are herein incorporated by reference.

Figure 3:
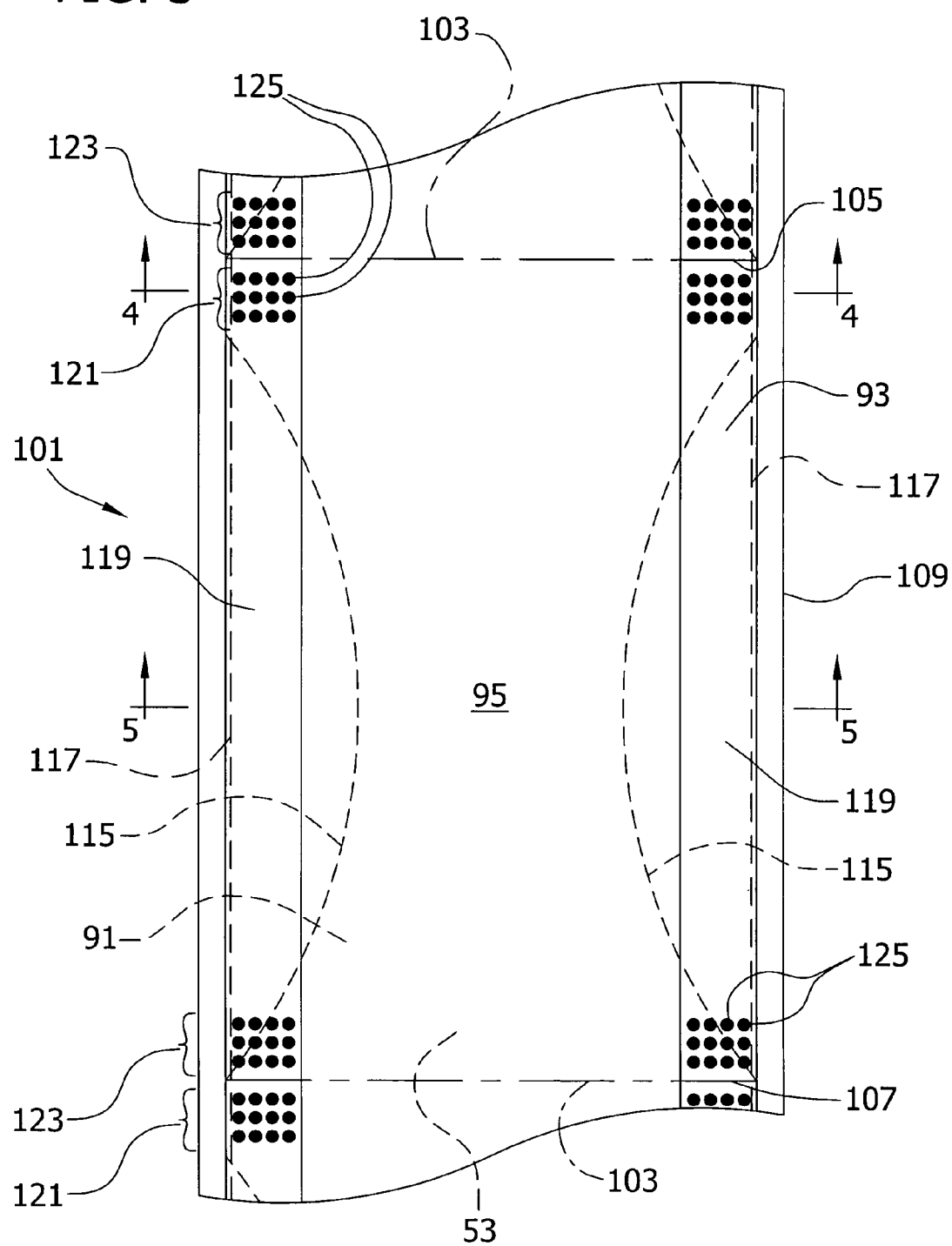
FIG. 3 is a fragmented plan view of a continuous absorbent structure web of the present invention.
Figure 4:
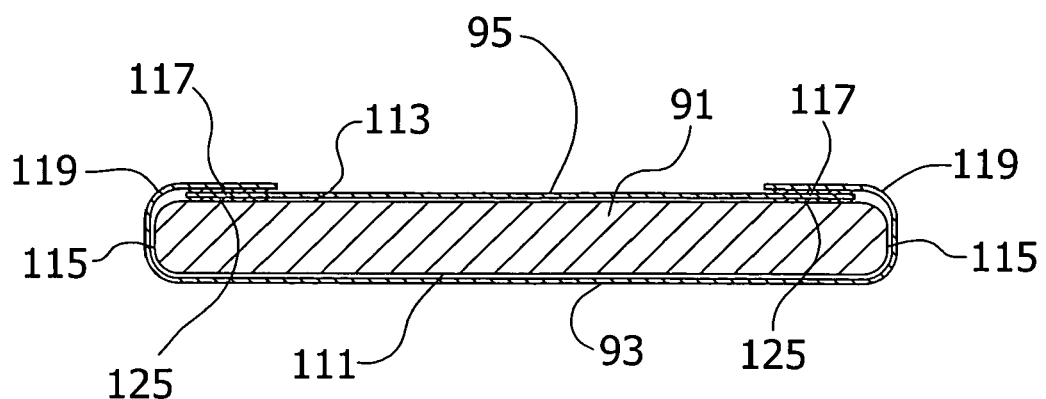
FIG. 4 is a cross-section taken in the plane of line 4-4 of FIG. 3.
Figure 5:
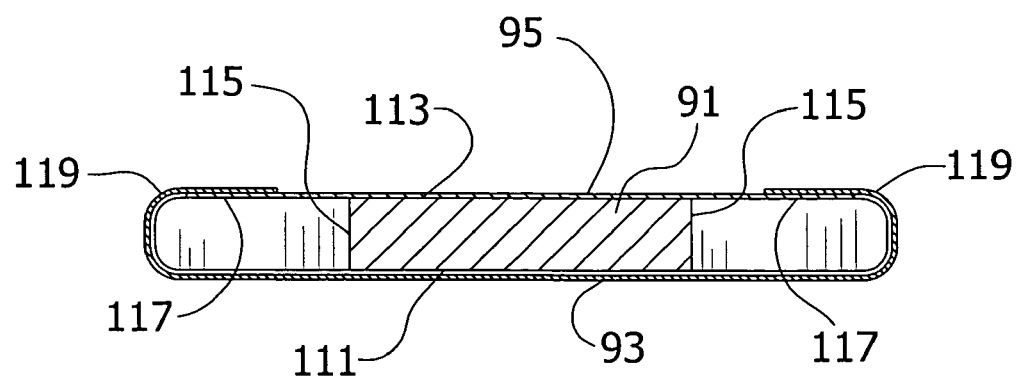
FIG. 5 is a cross-section taken in the plane of line 5-5 of FIG. 3.

In accordance with the present invention, the absorbent structure 53 suitably comprises an absorbent core 91 wrapped at least in part by a liquid permeable wrapsheet 93 as shown in FIGS. 3-5. The absorbent core 91 is suitably compressible, conformable, non-irritating to a wearer's skin, and capable of absorbing and retaining liquid body exudates. As an example, the absorbent core 91 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In one particular embodiment, the absorbent core 91 comprises a matrix of cellulosic fluff and superabsorbent material. One suitable type of fluff is identified with the trade designation CR 1654, available from U.S. Alliance of Childersburg, Ala., USA, and is a bleached, highly absorbent sulfate wood pulp containing primarily soft wood fibers.

The materials may be formed into a continuous or discrete web by employing various conventional methods and techniques. For example, the absorbent core 91 may be formed by a dry-forming technique, an air forming technique, a wet-forming technique, a foam-forming technique, or the like, as well as combinations thereof. Methods and apparatus for carrying out such techniques are well known in the art.

The absorbent core 91 may alternatively comprise a coform material. The term "coform material" generally refers to composite materials comprising a mixture or stabilized matrix of thermoplastic fibers and a second non-thermoplastic material. As an example, coform materials are made by a process in which at least one meltblown fiber die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

Furthermore, the absorbent core 91 may itself encompass multiple layers in a Z-direction (e.g., thickness) thereof. Such multiple layers may take advantage of differences in absorbent capacity, such as by placing a lower absorbent capacity material layer closer to the liner 51 and a higher absorbent capacity material closer to the outer cover 49. Likewise, portions of a single-layered absorbent core 91 may encompass higher capacity absorbents, and other portions of the core may encompass lower capacity absorbents.

Superabsorbent materials are well known in the art and can be selected from natural, synthetic, and modified natural polymers and materials. The superabsorbent materials can be inorganic materials, such as silica gels, or organic compounds, such as crosslinked polymers. The superabsorbent material is suitably capable of absorbing at least about 10 times its weight in liquid, and is more suitably capable of absorbing more than about 25 times its weight in liquid. The superabsorbent material concentration within the absorbent core is suitably in the range of about 10 to about 90 percent by weight of the absorbent core.

FIG. 3 particularly illustrates a continuous absorbent structure web 101, formed in accordance with a process described later herein, that is subsequently cut (e.g., at the cut lines 103 indicated in FIG. 3) into discrete absorbent structures 53 for placement in an absorbent article (e.g., diaper 21). The absorbent core 91 of the absorbent structure 53 shown in FIG. 3 is generally hour-glass shaped, i.e., narrowing in width from longitudinally opposite end regions 105, 107 of the absorbent structure 53 to a central region 109 thereof. It is understood, however, that the absorbent core 91 may be other than hour-glass shaped, such as rectangular, ovate, T-shaped, I-shaped or other suitable shape without departing from the scope of this invention.

The wrapsheet 93 is suitably pliable, less hydrophilic than the absorbent core 91 and sufficiently porous to be liquid permeable to thereby permit liquid to readily penetrate through its thickness to the absorbent core. The wrapsheet 93 also has sufficient structural integrity to withstand wetting thereof and of the absorbent core 91 wrapped by the wrapsheet. The wrapsheet 93 may be constructed from a single layer of material, or it may be a laminate constructed of two or more layers of material.

In a particularly suitable embodiment, the wrapsheet 93 is constructed of one or more layers of a non-woven web material, more suitably a non-woven web comprised at least in part of thermoplastic material, and even more suitably a meltblown web or layer. Meltblown webs or layers are made from fibers formed by extruding a molten thermoplastic material through a plurality of fine, usually circular dye capillaries as molten threads or filaments into a high-velocity heated air stream which attenuates the filaments of molten thermoplastic material to reduce their diameters. Thereafter, the meltblown fibers are carried by the high-velocity gas stream and are deposited on a collecting surface to form a web of randomly dispersed meltblown fibers. As one example, the wrapsheet 93 may be a laminate comprised of a meltblown nonwoven material layer consisting essentially of fine fibers, laminated to at least one, and more suitably laminated between two, spunbonded nonwoven material layers consisting essentially of coarser fibers (otherwise referred to herein as SM, which stands for spunbonded-meltblown material, and SMS, which stands for spunbonded-meltblown-spunbonded material).

The meltblown nonwoven material layer includes fibers having a suitable average diameter of less than about 5 microns, and more suitably less than about 2 microns and may be formed by conventional meltblown fiber making processes. Suitable well known meltblown fiber making processes are described in U.S. Pat. No. 3,849,241 to Butin et al. and U.S. Pat. No. 5,213,881 to Timmons et al., the disclosures of which are incorporated herein by reference. The basis weight of the meltblown layer is suitably less than or equal to about 1.5 grams per square meter (gsm), more suitably less than about 1 gsm, still more suitably less than about 0.8 gsm, and even more suitably less than about 0.5 gsm. In some embodiments the basis weight may be less than or equal to about 0.06 gsm.

The spunbonded nonwoven material layer includes filaments having a suitable average diameter in the range of from about 8 microns to about 30 microns, and more suitably in the range of from about 8 microns to about 25 microns. The spunbonded layer can be formed by conventional spunbonded fiber making processes. Suitable known spunbonded fiber making processes are described in, for example, U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. The basis weight of each spunbonded layer may be in the range of from about 4 gsm to about 30 gsm, and more suitably in the range of from about 10 gsm to about 20 gsm.

The meltblown layer and spunbonded layer(s) can be bonded together at intermittent locations therebetween for a total basis weight not to exceed about 55 gsm and the amount of meltblown fibers in the laminate based on the total weight of the laminate can be as low as 10 weight percent, as low as 5 weight percent and even as low as 1 weight percent. In particularly suitable embodiments, the total basis weight of the laminate is less than about 10 gsm with the fine meltblown fibers constituting in the range of about 5 percent to about 25 percent by weight of the total laminate weight.

The meltblown fibers suitably comprise thermoplastic resins including polyolefins having predominantly propylene polymer but which may include polyethylene or other alpha-olefins polymerized with Ziegler-Natta catalyst technology, and copolymers, terpolymers, or blends thereof. Thermoplastic fibers including polypropylene resins are suitable for the spunbonded layer. However, the spunbonded fibers can be made from inherently wettable, nonpolyolefin resins such as polymers and copolymers of vinyl acetate or lactic acid. Alternatively, the meltblown and/or spunbonded fibers or the layer formed thereof, can be treated with one or more surfactants to improve the wettability of the fibers and the resulting nonwoven web. Suitable examples of spunbonded-meltblown laminates and spunbonded-meltblown-spunbonded laminates formed from a fine meltblown fiber layer and a coarser spunbonded fiber layer (or layers) are described in copending U.S. application Ser. No. 10/657,498, filed Sep. 8, 2003 and entitled NONWOVEN FABRIC LAMINATE THAT REDUCES PARTICLE MIGRATION, the entire disclosure of which is incorporated herein by reference. Other examples of suitable wrapsheet material are disclosed in co-assigned U.S. Pat. No. 5,458,592 (Abuto, et al.), the entire disclosure of which is incorporated herein by reference.

It is also contemplated that the wrapsheet 93 may comprise a non-woven web constructed of materials other than thermoplastic materials. For example, the non-woven web may be a tissue web, or it may be a film having apertures formed therein, or it may be constructed of any of the materials disclosed above from which the bodyside liner 51 and/or outer cover 49 may be constructed, without departing from the scope of this invention.

With particular reference now to FIGS. 3-5, the wrapsheet 93 is suitably wrapped about at least one face of the absorbent core 91 as well as side edges 115 of the absorbent core. In particular, the wrapsheet 93 suitably covers at least the bodyside face 111 (i.e., that faces the wearer when the absorbent article is worn) of the absorbent core 91 and the side edges 115 of the absorbent core. The absorbent core 91 and wrapsheet 93 are shown in FIGS. 4 and 5 with the bodyside face 111 of the absorbent core facing downward (e.g., the lower face in FIGS. 4 and 5) in accordance with one method for wrapping the absorbent core as will be described later herein. In the illustrated embodiment, the wrapsheet 93 further extends over a lateral extent of the opposite face (the garment side face 113, i.e., that faces toward the garment of, or outward away from, the wear of the absorbent article) of the absorbent core 91 as shown in FIG. 4 such that a portion of the absorbent core between lateral side margins 119 of the wrapsheet remains unwrapped by the wrapsheet.

In the illustrated embodiment, a cover layer 95 (as best seen in FIGS. 4 and 5) overlays the garment side face 113 of the absorbent core 91 and extends laterally up to or slightly inward of the side edges 115 of the absorbent core to cover the portion of the absorbent core that is unwrapped by the wrapsheet 93. In a particularly suitable embodiment as shown in FIGS. 4 and 5, the lateral side margins 119 of the wrapsheet 93 overlay lateral side margins 117 of the cover layer 95, so that the lateral side margins of the cover layer are disposed between the wrapsheet and the absorbent core. However, it is contemplated that the lateral side margins 117 of the cover layer 95 may overlay the lateral side margins 119 of the wrapsheet 93 without departing from the scope of this invention.

As incorporated into an absorbent article 21, the cover layer 95 is disposed between the absorbent core 91 and the outer cover 49 of the article. In one particular embodiment, the cover layer 95 is suitably air permeable (e.g., breathable) but relatively liquid impermeable to inhibit liquid taken into the absorbent core 91 against contacting the outer cover 49 of the article. As an example, the cover layer 95 may be constructed of SM material, SMS material or other materials disclosed above from which the wrapsheet 93 may be constructed, but formed to be substantially less liquid permeable (e.g., having a higher density) than the wrapsheet. It is understood, however, that the cover layer 95 may be both liquid and air impermeable, or it may be liquid permeable, and remain within the scope of this invention. For example, other suitable materials from which the cover layer 95 may be constructed include, without limitation, a tissue web, a film with or without apertures formed therein, or any of the materials described previously from which the liner 51 or the outer cover 49 may be constructed.

Because the absorbent core 91 is substantially narrower at the central region 109 of the absorbent structure 53 than at the longitudinal end regions 105, 107 thereof, the wrapsheet 93 generally extends in opposed relationship with itself free of any interposing absorbent core along the central region of the absorbent structure as shown in FIGS. 3 and 5, while still wrapping about the absorbent core side edges 115 at the longitudinal end regions 105, 107 of the absorbent structure. As shown in the illustrated embodiment, the lateral side margins 117 of the cover layer 95 may still extend between the opposed portions of the wrapsheet 93 along the central region 109 of the absorbent structure, as long as no absorbent core material extends between the opposed portions of the wrapsheet.

It is understood that the cover layer 95 may be omitted from the various embodiments shown in the drawings and described herein without departing from the scope of this invention. In such an embodiment, the unwrapped portion of the garment side face 113 of the absorbent core 91 would be exposed and face the outer cover 49 of the article in use. It is also contemplated that the wrapsheet 93 may instead wrap fully about the absorbent core 91, and may even overlap itself (e.g., by extending slightly greater than once around the core so that an overlapped portion overlies and underwrapped portion thereof), without departing from the scope of this invention.

The wrapsheet 93 is suitably secured to the absorbent core 91, and more particularly to both the cover layer 95 and the absorbent core as shown in the illustrated embodiment, to secure the wrapsheet against unintended unwrapping of the wrapsheet away from the absorbent core. In the illustrated embodiment of FIG. 3, the wrapsheet 93 is secured to the cover layer 95 and absorbent core 91 generally at the longitudinal end regions 105, 107 of the absorbent structure 53, and even more particularly the wrapsheet is secured to the cover layer and absorbent core at laterally spaced securement regions 121, 123 disposed at the respective longitudinal end regions 105, 107 of the absorbent structure. A portion of the securement region 121 at one end region 105 of the absorbent structure 53 extends out beyond the side edge 115 of the absorbent core such that the wrapsheet is additionally secured to the cover layer and to itself within that securement region (e.g., free of intervening absorbent core material). The wrapsheet 93 is otherwise free from securement to the cover layer 95 and absorbent core 91 or to the cover layer and to itself along the longitudinal extent of the absorbent structure 53 extending longitudinally intermediate the securement regions 121, 123, and more particularly along the central region 109 (e.g., which generally corresponds to the crotch region 27 of the diaper 21) of the absorbent structure.

It is contemplated that where the lateral side margins 119 of the wrapsheet 93 extend further inward of the absorbent core side edges 115 over the garment side face 113 of the absorbent core 91, including where the wrapsheet extends fully about the absorbent core, the wrapsheet may be secured to the absorbent core (and to the cover layer 95 when present) other than at laterally spaced securement regions 121, 123. For example, two longitudinally spaced (and laterally central) securement regions may be used, or more closely laterally spaced securement regions may be used, and remain within the scope of this invention. Securing the wrapsheet to the absorbent core 91 at discrete securement regions, e.g., instead of along the length of the absorbent structure 53, maintains some of the flexibility of the absorbent structure which would otherwise be stiffened by securing the wrapsheet to the absorbent core along the length of the absorbent structure.

In a particularly suitable embodiment, the wrapsheet 93 is autogenously secured to the absorbent core 91 (and cover layer 95 when present). As used herein, autogenous securement refers to direct securement without the use of additional securing materials (e.g., in addition to the wrapsheet, cover layer and absorbent core materials themselves), such as an adhesive layer, fasteners or the like. Pressure bonding, ultrasonic bonding and thermal bonding are some examples of suitable autogenous securement techniques. Pressure bonding is a conventional bonding technique known to those skilled in the art and will not be described in detail herein other than to the extent necessary to describe the present invention. As an example, in the manufacturing apparatus shown in FIG. 10, pressure bonding is effected by passing the unbonded wrapsheet 93, cover layer 95 and core 91 together (at least at the desired locations of the securement regions) to a bonding apparatus, generally indicated at 285, such as a conventional debulking apparatus having a nip formed between a pair of rolls 287. One of the rolls 287 may have a pattern of discrete, raised points on its surface to define a bonding pattern whereby the wrapsheet becomes bonded to the absorbent core at discrete points in the prescribed bonding pattern. In the illustrated embodiment the bonding pattern comprises discrete bond points 125 arranged to define a generally rectangular securement region 121, 123. However, the bond pattern may be other than that shown in FIG. 3, such as any of the bond patterns shown in FIGS. 6*a-e*, combinations thereof, or other suitable bond patterns. It is contemplated that one or both of the rolls may be heated to facilitate bonding. It is also contemplated that the rolls may be planar (e.g., patternless) such that the wrapsheet 93 is bonded to the absorbent core 91 (and/or another portion of the wrapsheet) throughout substantially the entire securement region.

In the particular embodiment shown in FIG. 3, the wrapsheet 93 of the absorbent structure web 101 is bonded to the cover layer 95 and absorbent core 91 at a location corresponding to the trailing longitudinal end region 107 of one absorbent structure 53 and the leading longitudinal end region 105 of the following absorbent structure 53 upon a single passing of the absorbent structure web through the pressure nip. Bonding the wrapsheet 93 to the absorbent core 91 at the longitudinal end regions 107, 105 of consecutive absorbent structures 53 in a web 101 thereof in this manner reduces the risk of unwrapping of the wrapsheet away from the absorbent core upon cutting of the web into discrete absorbent structures along the indicated cut lines 103.

Figure 8:
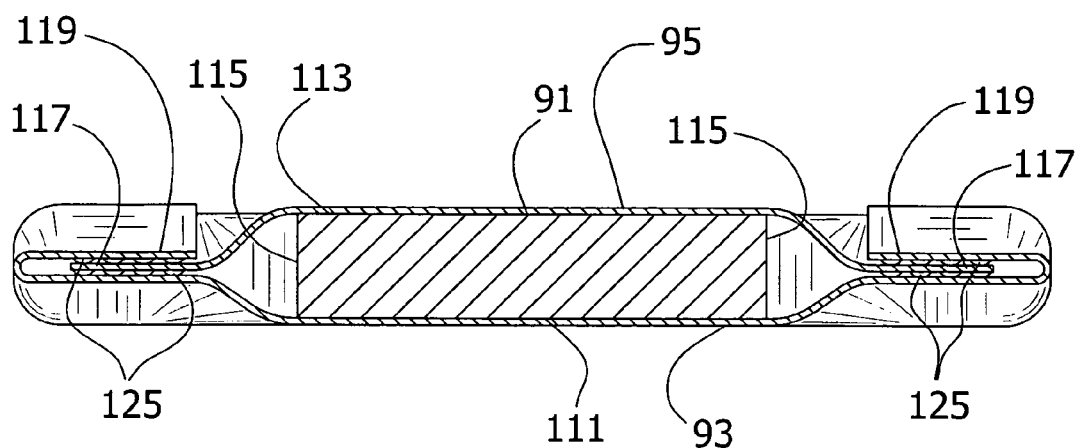
FIG. 8 is a cross-section taken in the plane of line 8-8 of FIG. 7.
Figure 9:
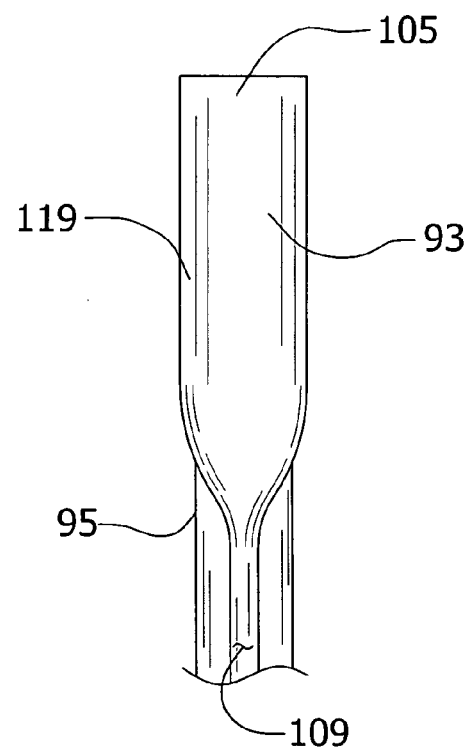
FIG. 9 is a partial side elevation taken in the plane of the line 9-9 of FIG. 7.

In another embodiment, shown in FIGS. 7-9, the wrapsheet 93 is instead secured, and more suitably bonded in the manner described above, to the cover layer 95 and to itself at a securement region 131 extending longitudinally along the central region 109 of the absorbent structure 53, i.e., where the wrapsheet does not wrap about the side edges 115 of the core 91 (while still wrapping about the side edges at the longitudinal ends 105, 107 of the absorbent structure), or otherwise stated where the wrapsheet is folded over free from any interposing absorbent core material. Such an embodiment eliminates the need to bond the wrapsheet 93 through the thickness of the absorbent core 91, concentrating the bonding energy instead only in areas of the wrapsheet devoid of absorbent core material.

Figure 10:
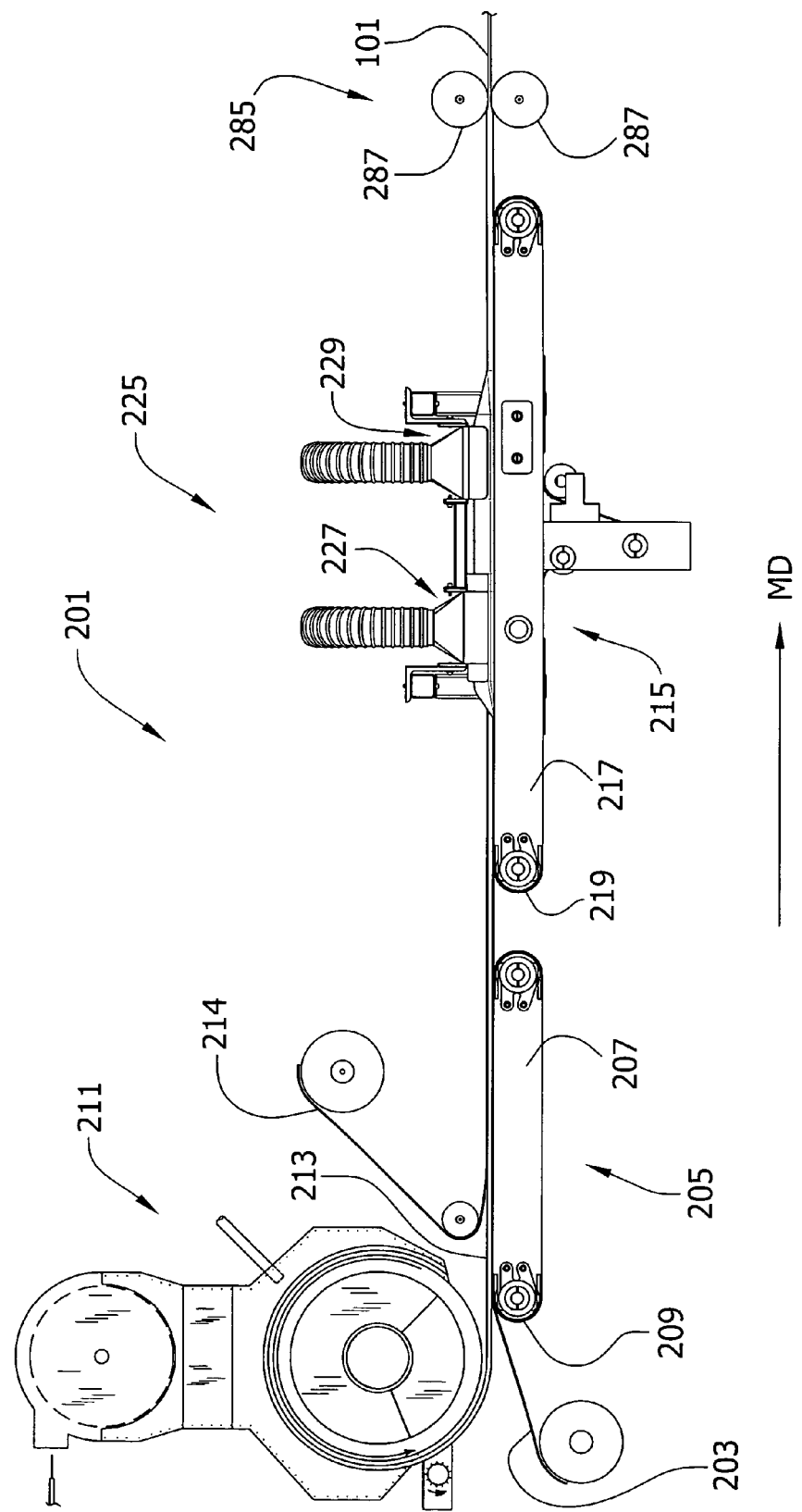
FIG. 10 is a schematic side elevation of one embodiment of apparatus of the present invention for making an absorbent structure in which a wrapsheet is wrapped about an absorbent core.

FIGS. 10-16 illustrate one embodiment of apparatus, generally indicated at 201, for making an absorbent structure such as the absorbent structure 53 described above as comprising an absorbent core 91 wrapped at least in part by a wrapsheet 93. With particular reference to FIG. 10, a continuous web 203 of wrapsheet material is carried by a suitable conveying apparatus, generally indicated at 205, such as the type comprising a vacuum box 207 and a continuous foraminous belt 209 moved continuously over the vacuum box, past an absorbent core making apparatus 211.

It is understood that other suitable conveying apparatus may be used, or that no conveying apparatus may be used and the web 203 of wrapsheet material fed unsupported past the absorbent core making apparatus 211, without departing from the scope of this invention. Suction from the vacuum box 207 holds the wrapsheet web 203 generally flat down against the foraminous belt 209 for movement therewith. A continuous web 213 of absorbent core material is formed by the core making apparatus 211 and laid in a laterally central position on the moving web 203 of wrapsheet material and retained thereon by suction from the vacuum box 207 such that the wrapsheet web and overlying absorbent core web are conveyed together by the conveying apparatus 205 downstream of the absorbent core making apparatus in a machine direction (MD) of manufacture. As used herein, the term "machine direction" refers to the direction of movement of the absorbent structure web 101, or components thereof (e.g., the wrapsheet web 203 and absorbent core web 213), during manufacture. The "cross-machine direction" (CD) refers to the direction transverse to the machine direction and generally in the plane of the absorbent structure web 101 or components thereof.

The core making apparatus 211 shown in FIG. 10 is a conventional airforming apparatus, the operation and construction of which is known to those skilled in the art and will not described herein except to the extent necessary to set forth the present invention. It also understood that the web 213 of absorbent core material may be made other than by airforming apparatus, such as by airlaying apparatus, coforming apparatus or other suitable forming apparatus and remain within the scope of this invention. It is also contemplated that discrete absorbent cores 91 (e.g., instead of a continuous web 213 of core material) may be made by the core making apparatus 211 and laid on the moving web 203 of wrapsheet material. In other embodiments, the wrapsheet web 203 may be fed to the core making apparatus whereby discrete absorbent cores are formed directly on the continous wrapsheet web. Downstream of the core making apparatus 211, a continuous web 214 of cover layer material is laid onto the moving web 213 of absorbent core material.

The continuous web 203 of wrapsheet material and overlying web 213 of absorbent core material and web 214 of cover layer material are transferred onto another conveying apparatus 215 comprising a vacuum box 217 and an continuous foraminuous belt 219 having an upper reach 221 (FIG. 11) that moves over the vacuum box. It is understood, though, that a single conveying apparatus may be used instead of the two conveying apparatus 205, 215 and remain within the scope of this invention.

Figure 11:
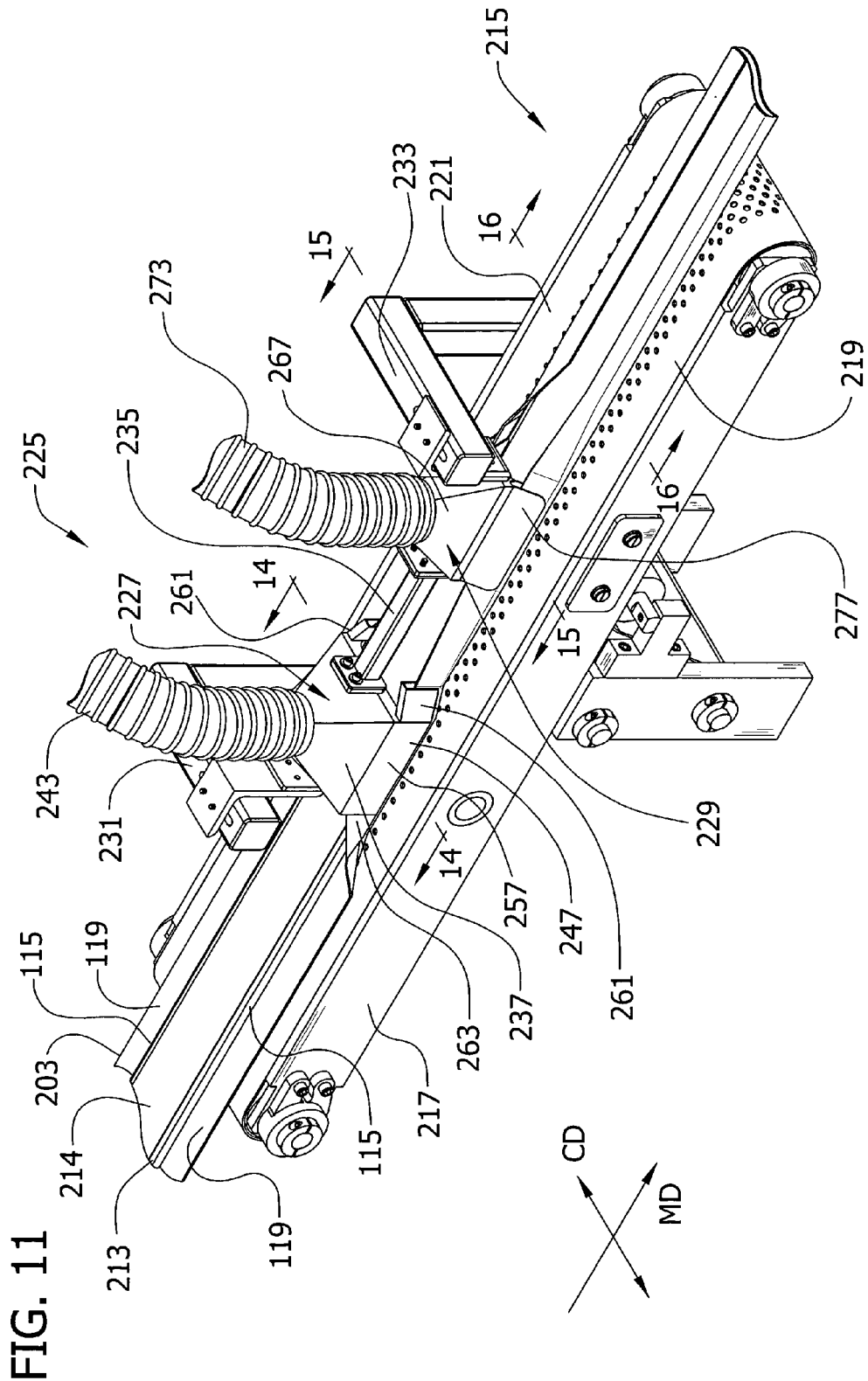
FIG. 11 is a perspective of one embodiment of wrapping apparatus of the present invention for wrapping the wrapsheet about the absorbent core.
Figure 12:
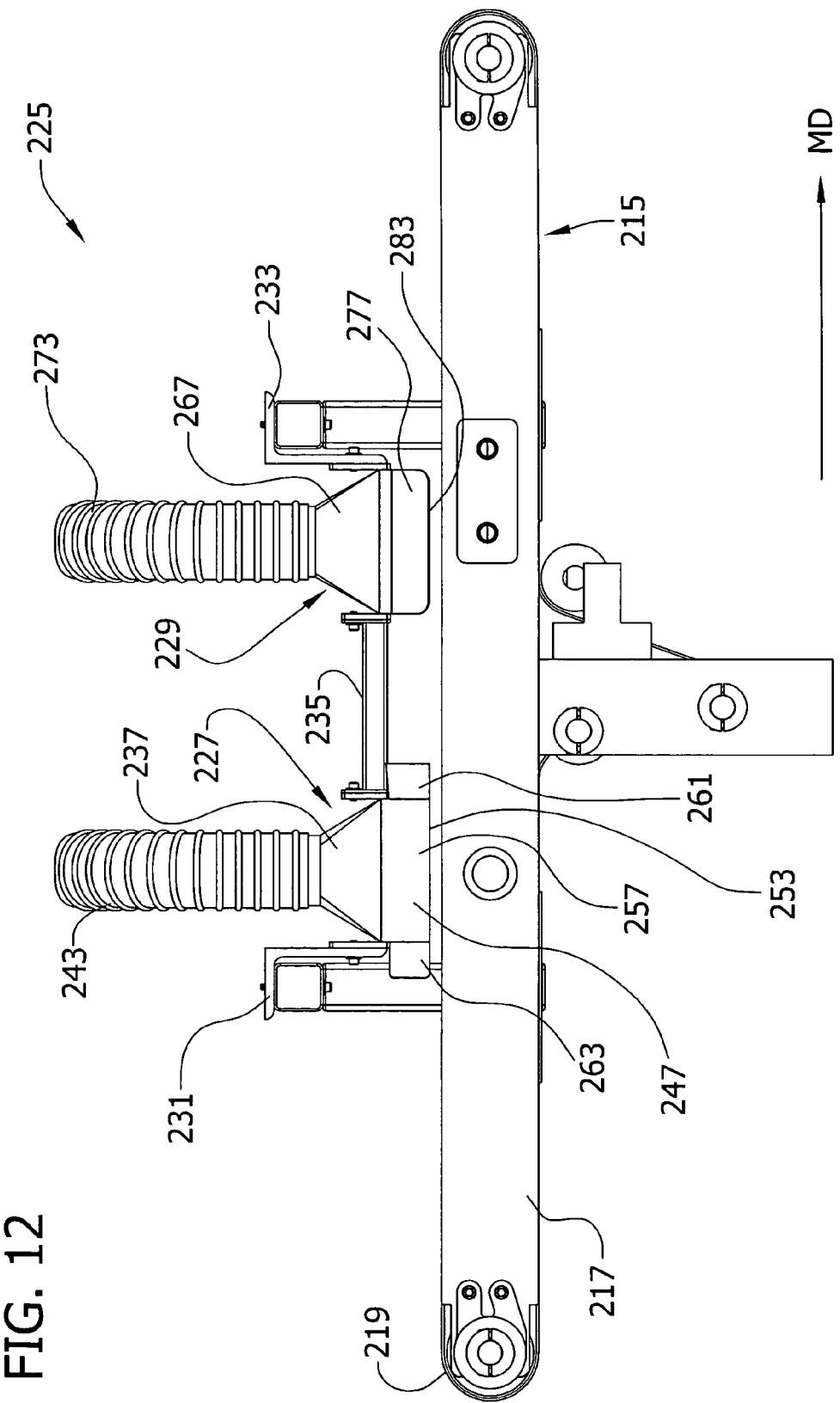
FIG. 12 is a side elevation of the wrapping apparatus of FIG. 11, with the wrapsheet, absorbent core and a cover layer omitted.

As can be seen in FIG. 11, the width of the absorbent core web 213 is substantially less than the width of the wrapsheet web 203 when both are laid flat and held down against the moving belt 219, with the cover layer web 214 having a width slightly less than the width of the absorbent core web. The conveying apparatus 215 conveys the wrapsheet web 203, absorbent core web 213 and cover layer web 214 together to wrapping apparatus, generally indicated at 225, of the present invention which draws the lateral side margins 119 of the wrapsheet web 203 (e.g., the portion of the wrapsheet web that extends laterally outward from the side edges 115 of the absorbent core web 213 to the side edges of the wrapsheet web) up from the foraminous belt 219 and wraps the wrapsheet web about the cover layer web and absorbent core web without the use of mechanical folding structure such as folding skis, folding boards, folding bars, etc. Rather, as will be described in further detail, the wrapsheet web 203 is wrapped about the absorbent core web 213 and cover layer web 214 using gas (e.g., air) flow, and more particularly using pressurized gas such as by a vacuum, to minimize or even inhibit contact of the wrapsheet web with the wrapping apparatus 225 during wrapping and to eliminate the need for mechanical structure such as folding boards or other folding structure.

The wrapping apparatus 225 of the illustrated embodiment comprises first and second vacuum units indicated generally at 227 and 229, respectively, spaced apart from each other in the machine direction, i.e., the direction of movement of the wrapsheet, absorbent core and cover layer webs 203, 213, 214. The first vacuum unit 227 is mounted by suitable framing structure 231 to one side of the vacuum box 217 for disposition above the upper reach 221 of the foraminous belt 219 so that the vacuum unit is laterally positioned centrally of the moving webs 203, 213, 214. The vacuum unit 227 is adjustably held by the framing structure 231 to allow adjustment of the cross-machine (e.g., lateral) position of the first vacuum unit relative to the conveying apparatus 225 (e.g., relative to the web assembly). The second vacuum unit 229 is secured by additional framing structure 233 to the one side of the vacuum box 217 in substantially the same manner as the first vacuum unit 227 but downstream therefrom in the machine direction. An intermediate frame member 235 extends longitudinally (e.g., in the machine direction) between and interconnects the two vacuum units 227, 229.

It is understood that the particular framing structure used and the manner in which the vacuum units 227, 229 are located and retained in their respective positions above the conveying apparatus 215 is not important to the present invention other than that each vacuum unit be retained at a predetermined height above the conveying apparatus and at a predetermined cross-machine position relative to the width of the conveying apparatus. That is, many other frame structures and configurations may be used to retain the vacuum units 227, 229 at a predetermined height and position without departing from the scope of this invention. For example, with reference to FIG. 11, the framing structure 231, 233 need not be secured to the conveying apparatus 225. For example, the framing structure 231, 233 may hang down from overhead supports (not shown), may free stand from the floor to above the conveying apparatus 215, or supported in some other manner without departing from the scope of this invention. It is also contemplated that the additional frame member 235 interconnecting the vacuum units 227, 229 may be omitted.

Figure 13:
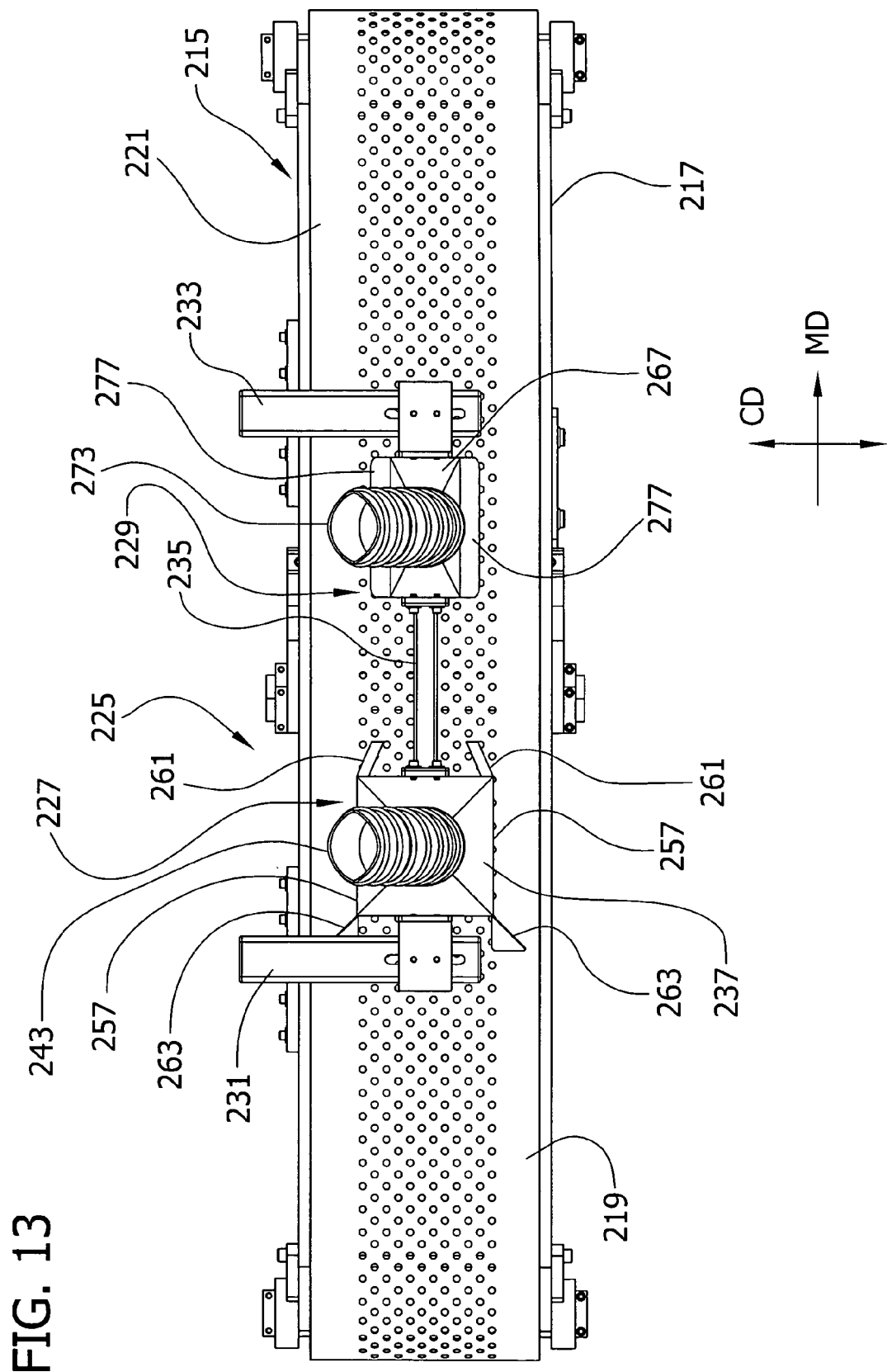
FIG. 13 is a top plan view of the wrapping apparatus of FIG. 11, with the wrapsheet, absorbent core and cover layer omitted.
Figure 14:
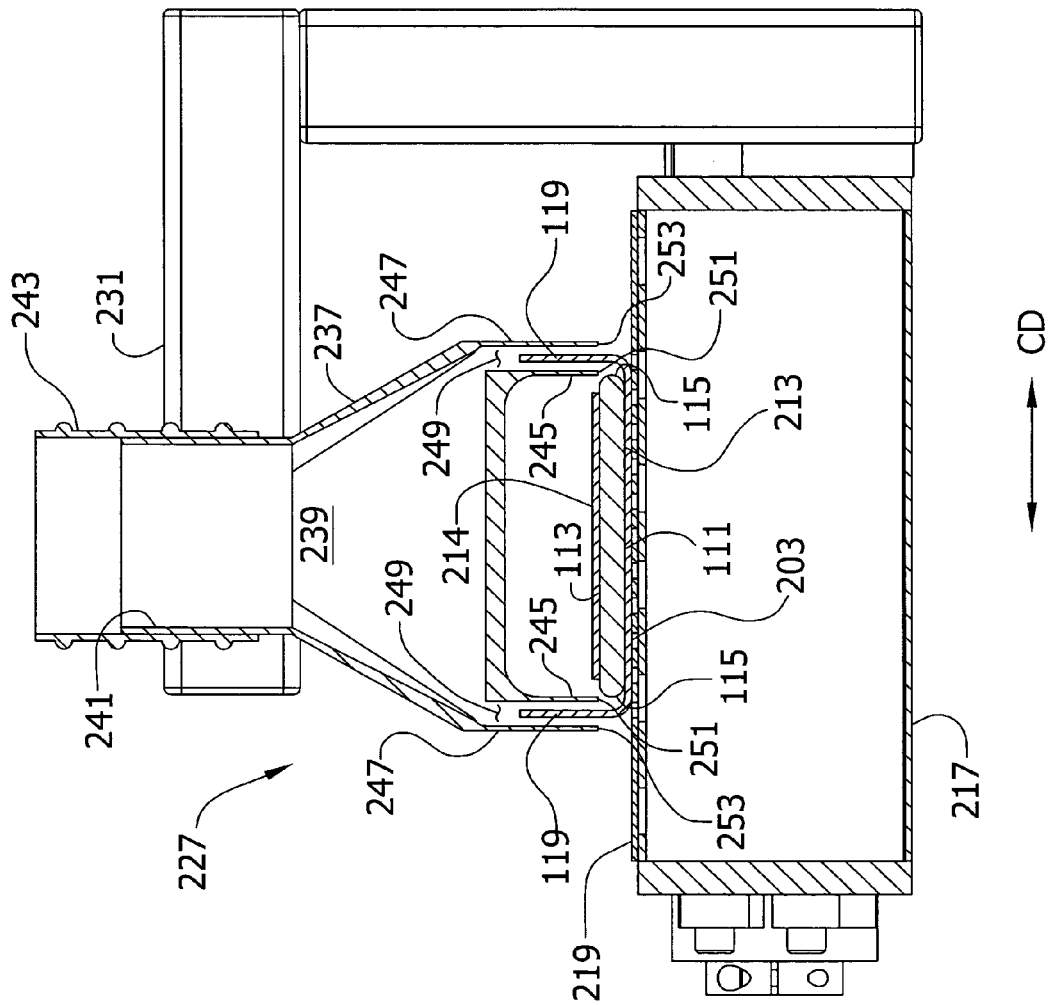
FIG. 14 is a cross-section taken in the plane of line 14-14 of FIG. 11, with portions of the apparatus upstream of line 14-14 omitted.

As shown in FIGS. 11-16, and with particular reference to FIG. 14, the first vacuum unit 227 generally comprises a housing section 237 defining an interior vacuum chamber 239 therein. The housing section 237 has a vacuum inlet 241 to which a suitable vacuum conduit 243 is connected to provide fluid communication between the vacuum chamber and a source of vacuum (not shown), such as a vacuum pump or other suitable vacuum generating device. The vacuum pressure provided by the first vacuum unit 227 is sufficient to lift the lateral side margins 119 of the wrapsheet web 203 up off of the foraminous belt 219 (e.g., overcoming the suction from the vacuum box 217). For example, the vacuum pressure provided by the first vacuum unit 227 may suitably be in the range of about 5.1 cm (about 2 inches) to about 38.1 cm (about 15 inches) of water, more suitably about 5.1 cm to about 22.9 cm (about 9 inches), and even more suitably about 5.1 cm to about 18 cm (about 7 inches). In general, a lower vacuum pressure and higher airflow is preferred over a higher vacuum pressure and lower airflow.

A pair of inner fins 245 depend from the housing section 237 in laterally spaced relationship with each other. A pair of laterally spaced outer fins 247 also depend from the housing section 237, with each outer fin being spaced laterally outward from a respective one of the inner fins 245 such that each pair of opposed inner and outer fins defines a vacuum slot 249 therebetween. In the illustrated embodiment, the outer fins 247 are generally parallel to the inner fins 245. However, it is contemplated that the fins 247, 245 may not be parallel to each other, e.g., the fins may spaced further from each other at bottom edges thereof and be spaced closer together (e.g., the width of the vacuum slots 249 decreases) toward the vacuum chamber 239), without departing from the scope of this invention. The vacuum slots 249 are open to the vacuum chamber 239 to provide fluid communication between the vacuum slots and the source of vacuum.

In the illustrated embodiment, the inner and outer fins 245, 247 of the first vacuum unit 227 are oriented generally perpendicular (e.g., 90 degrees) to the plane defined by the machine direction and cross-machine direction of the continuous webs 203, 213 of wrapsheet and absorbent core material such that the vacuum slots 249 defined by the inner and outer fins have a perpendicular angular orientation (e.g., a vertical orientation in the illustrated embodiment) relative to the plane of the absorbent core web. It is contemplated that the angular orientation of the vacuum slots 249 relative to the absorbent core web may be other than 90 degrees as in the illustrated embodiment without departing from the scope of this invention. For example, the angular orientation of the vacuum slots 249 relative to the absorbent core web may suitably be in the range of about 150 degrees to about 30 degrees (with an angle of less than 90 degrees meaning a generally laterally outward slanting of the slots and an angle of greater than 90 degrees meaning a generally laterally inward slanting of the slots), and more suitably in the range of about 60 degrees to about 120 degrees.

Bottom edges 251, 253 (FIG. 14) of the fins 245, 247 define inlets to the vacuum slots 249, and are suitably disposed above the foraminous conveyor belt 219 in the range of about 0.125 to about 2 inches (about 3 to about 51 mm), more suitably 0.125 inches to about 1 inch (about 3 to about 25 mm), even more suitably about 0.25 inches to about 1 inch (about 6 to about 25 mm), and still more suitably about 0.5 inches (about 13 mm). The spacing between the inner and outer fins 245, 247 (e.g., the width of the vacuum slot 249) is suitably in the range of about 0.25 to about 0.5 inches (about 6.5 to about 13 mm).

A central portion 257 (best seen in FIG. 12) of the inner and outer fins 245, 247 (and hence the slot 249) extends in the machine direction MD along the length of the housing. The inner fins 245 are spaced laterally (e.g., in the cross-machine direction) from each other at the central portion 257 thereof a distance suitably about equal to or slightly less than the maximum width of the absorbent core web 213 (e.g., at the longitudinal end regions 105, 107 of the absorbent structure 53 of FIG. 3). However, the spacing between the inner fins 245 may be slightly greater than the maximum width of the absorbent core web 213 and remain within the scope of this invention. Stated another way, the distance between the centerlines of the vacuum slots 249 at the bottom edges 251, 253 of the fins 245, 247 is in the range of about 75 percent to about 125 percent of the maximum width of the absorbent core web 213, and more suitably in the range of about 90 percent to about 110 percent.

A downstream portion 261 of the inner and outer fins 245, 247 extends downstream from the central portion 257 thereof beyond the housing section 237, with the spacing between inner and outer fins (e.g., the vacuum slot width) remaining unchanged. However, as shown in the illustrated embodiment the inner and outer fins 245, 247 are angled laterally inward relative to vertical at the downstream portion 261, such as at an angle of about 15 degrees, relative to the central portion 257 for reasons which will be discussed later herein. The lateral spacing between the inner fins 245 at the downstream portion 261 (e.g., at the exit from the vacuum slot 249 at the downstream portion of the inner and outer fins) is suitably equal to or less than the maximum width of the web 213 of absorbent core material. As an example, in the illustrated embodiment the web 213 of absorbent core material may have a maximum width of about 5.2 inches (about 133 mm) and be laterally centered on a web of wrapsheet material (e.g., such as the SMS material described previously) having a width of about 7.9 inches (about 200 mm). The inner fins 245 of the first vacuum unit 227 are laterally spaced from each other at the central portion 257 thereof a distance of about 4.75 inches (about 121 mm), and are laterally spaced from each other at the downstream portion 261 thereof a distance of less than 4.75 inches (121 mm).

As seen best in FIGS. 11 and 13, a guide member 263 is attached to the upstream end of each of the outer fins 247. The guide members 263 are angled generally laterally outward of (e.g. wider apart than) the vertically oriented fins and are also gradually canted as they extend forward from the upstream ends of the outer fins to direct air drawn into the vacuum slots 249 to flow over the guide members toward the vacuum slots. While not shown in the drawings, a cover plate or other covering structure may be disposed between the belt 219 and the vacuum box 217 generally below the side margins 119 of the web 203 of wrapsheet material at the wrapping apparatus 225, i.e., laterally outward of the first and second vacuum units 227, 229, to reduce or block altogether the suction of the side margins of the wrapsheet against the belt.

The second vacuum unit 229 comprises a housing section 267, vacuum chamber 269, vacuum inlet 271 (FIG. 15), and conduit 273 similar to the first vacuum unit 227. The second vacuum unit 229 is in fluid communication with a source of vacuum (not shown), such as a vacuum pump or other suitable device, different from the source of vacuum used to draw a vacuum on the first vacuum unit 227. However, it is understood that the first and second vacuum units 227, 229 may be operably connected to the same source of vacuum without departing from the scope of this invention. The vacuum pressure provided by the second vacuum unit 229 may suitably be in the range of about 5.1 cm (about 2 inches) to about 38.1 cm (about 15 inches) of water, more suitably about 5.1 cm to about 22.9 cm (about 9 inches), and even more suitably about 5.1 cm to about 18 cm (about 7 inches). In general, a lower vacuum pressure and higher airflow is preferred over a higher vacuum pressure and lower airflow. It is also contemplated that the vacuum pressure provided by the second vacuum unit 229 may be greater or less than the vacuum pressure provided by the first vacuum unit 227 and remain within the scope of this invention.

Figure 15:
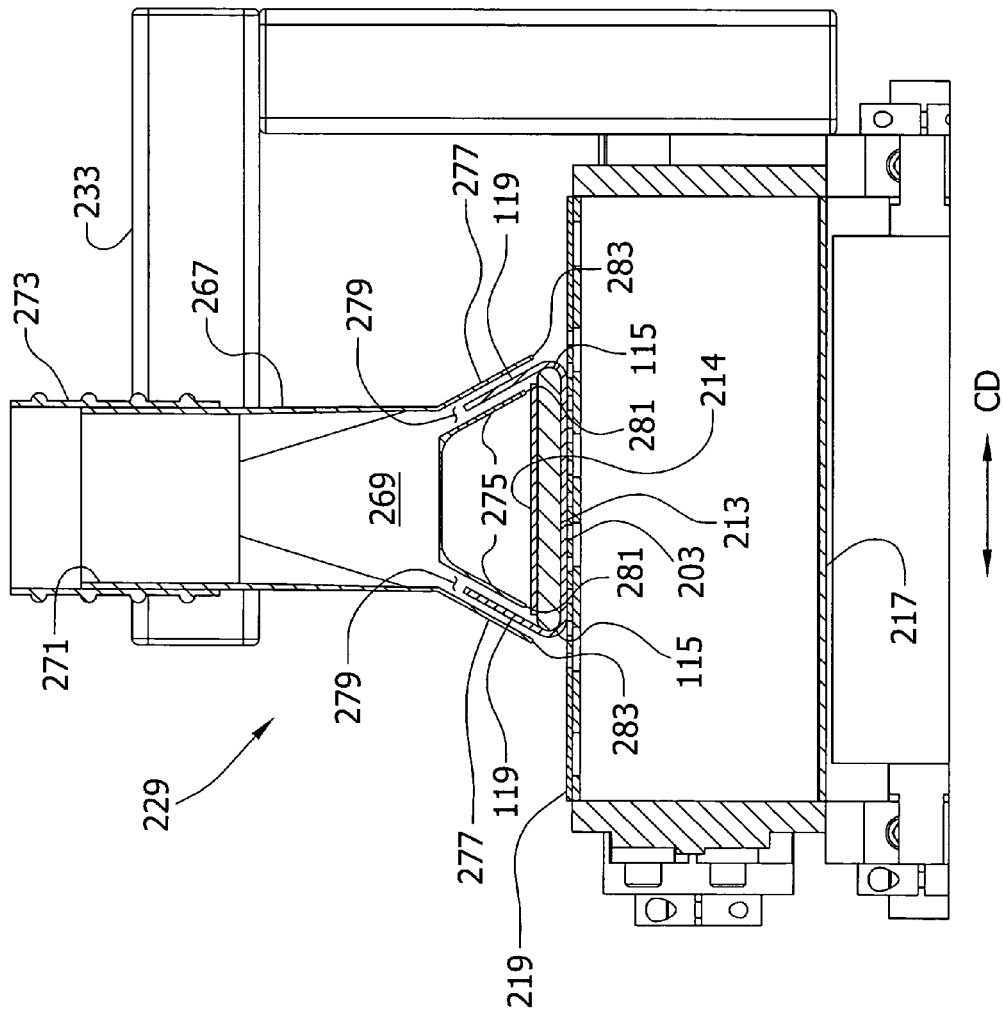
FIG. 15 is a cross-section taken in the plane of line 15-15 of FIG. 11, with portions of the apparatus upstream of line 15-15 omitted.

As shown in FIG. 15, the second vacuum unit 229 further comprises a pair of inner fins 275 depending from the housing section 267 in laterally spaced relationship with each other. A pair of laterally spaced outer fins 277 also depend from the housing section 267, with each outer fin being spaced laterally outward from a respective one of the inner fins 275 such that each pair of opposed inner and outer fins defines a vacuum slot 279 therebetween. The vacuum slots 279 are open to the vacuum chamber 269 to provide fluid communication between the vacuum slots and the source of vacuum.

In the illustrated embodiment, the inner and outer fins 275, 277 of the second vacuum unit 229 are suitably oriented at an angle relative to the plane of the absorbent core web 213, e.g., the plane defined by the machine direction and cross-machine directions. In this manner, the vacuum slots 279 defined by the inner and outer fins 275, 277 have an angular orientation relative to the belt 219 (and more particularly to the absorbent core web 213 carried by the belt) for reasons which will become apparent. For example, in the illustrated embodiment, the inner and outer fins 275, 277 (and therefore the vacuum slots) are oriented at an angle relative to the absorbent core web 213 of about 67.5 degrees. However, it is contemplated that the inner and outer fins 275, 277 (and therefore the slots 279) may suitably be oriented at any angle in the range of about 120 degrees to about 20 degrees relative to the absorbent core web 213, and more suitably in the range of about 60 degrees to about 90 degrees, and remain within the scope of this invention. It is also contemplated that the angle of one of the vacuum slots 279 relative to the web 213 may be different from the angle of the laterally opposite vacuum slot relative to the core web and remain within the scope of this invention.

Bottom edges 281, 283 of the fins 275, 277 define vacuum slot inlets and are suitably disposed above the foraminous conveyor belt 219 in the range of about 0.125 to about 2 inches (about 3 to about 51 mm), more suitably 0.125 inches to about 1 inch (about 3 to about 25 mm), even more suitably about 0.25 inches to about 1 inch (about 6 to about 25 mm), and still more suitably about 0.5 inches (about 13 mm). The spacing between the inner and outer fins 275, 277 (e.g., the width of the vacuum slot 279) is suitably in the range of about 0.25 to about 0.5 inches (about 6.5 to about 13 mm). The bottom edges 281 of the inner fins 275 (e.g., at the inlet to the vacuum slot 279) are spaced laterally (e.g., in the cross-machine direction) from each other a distance suitably equal to, and more suitably less than, the maximum width of the absorbent core web 213 to facilitate a relatively tight wrapping of the wrapsheet about the core. Stated another way, the distance between the centerlines of the vacuum slots 279 at the bottom edges of the fins 275, 277 is in the range of about 75 percent to about 125 percent of the maximum width of the absorbent core web 213, and more suitably in the range of about 90 percent to about 110 percent.

In operation, with reference to FIGS. 11-16, as the wrapsheet web 203 and overlying absorbent core web 213 and cover layer web 214 are conveyed by the conveying apparatus 215 to the wrapping apparatus 225, the wrapsheet web side margins 119 (e.g., the wrapsheet web portions that extend laterally outward beyond the side edges of the absorbent core web) approach the the upstream guide members 263 of the first vacuum unit 227. Air is drawn by the first vacuum unit 227 over the guide members toward the vacuum slots 249. The lateral side margins 119 of the wrapsheet web follow the air flow and are raised slightly off of the guide members (e.g., by the air flow) so that the side margins start to fold upward toward the angular orientation of the vacuum slots 249. As the side margins 119 of the wrapsheet web 203 enter the vacuum slots 249, the wrapsheet web side margins 119 are drawn up into the slots so that the side margins of the wrapsheet web become oriented generally perpendicular to the absorbent core web 213 along the opposite side edges 115 of the absorbent core web.

FIG. 14 is a cross-section taken transversely through the first vacuum unit 227 and illustrates the wrapsheet web side margins 119 being drawn taut and pulled up into the vacuum slots 249. Air is drawn into the slots 249 and flows over both faces of the wrapsheet web side margins 119 inhibits the side margins of the wrapsheet web against contact with the inner and outer fins 245, 247 that define the vacuum slots 249. The term inhibited as used herein means that the air flow generally biases the side margins 119 out of contact with the fins 245, 247, it being understood that the side margins 119 may have incidental (e.g., unintended) contact with the fins due to fluttering of the side margins within the vacuum slots 249). Pulling the wrapsheet web side margins 119 taut in this manner reduces and inhibits wrinkles in the wrapsheet and facilitates a tight wrapping of the wrapsheet web 203 about the absorbent core web 213.

As the wrapsheet web side margins 119 approach the downstream portion 261 of the fins 245, 247, the wrapsheet web side margins 119 are directed generally laterally inward by the laterally inward angled orientation of the downstream portion of the inner and outer fins. Directing the wrapsheet web side margins 119 laterally inward in this manner is intended to more closely align the lateral position of the wrapsheet web side margins with the upstream end of the inner and outer fins 275, 277 of the second vacuum unit 229. Upon entering the vacuum slots 279 defined by the inner and outer fins 275, 277 of the second vacuum unit 229, the side margins 119 of the wrapsheet web 203 are drawn into the vacuum slots and pulled taut at a more laterally inward directed angular orientation relative to the absorbent core web 213.

FIG. 15 is a cross-section taken transversely through the second vacuum unit 229 and illustrates the further inward pulling of the wrapsheet web side margins 119 by the second vacuum unit. As in the first vacuum unit 227, air is drawn into the slots 279 of the second vacuum unit 229 over both faces of the wrapsheet web side margins 119 to inhibit the side margins of the wrapsheet web against contact with the inner and outer fins 275, 277. Because the lateral spacing between the inner fins 275 is equal to or less than the maximum width of the absorbent core web 213, the side margins 119 of the wrapsheet web 203 are pulled taut against (i.e., wrapped generally tightly about) the side edges of the absorbent core web (e.g., at those portions of the absorbent core web having a width greater than or equal to the lateral spacing between the inner fins).

Figure 16:
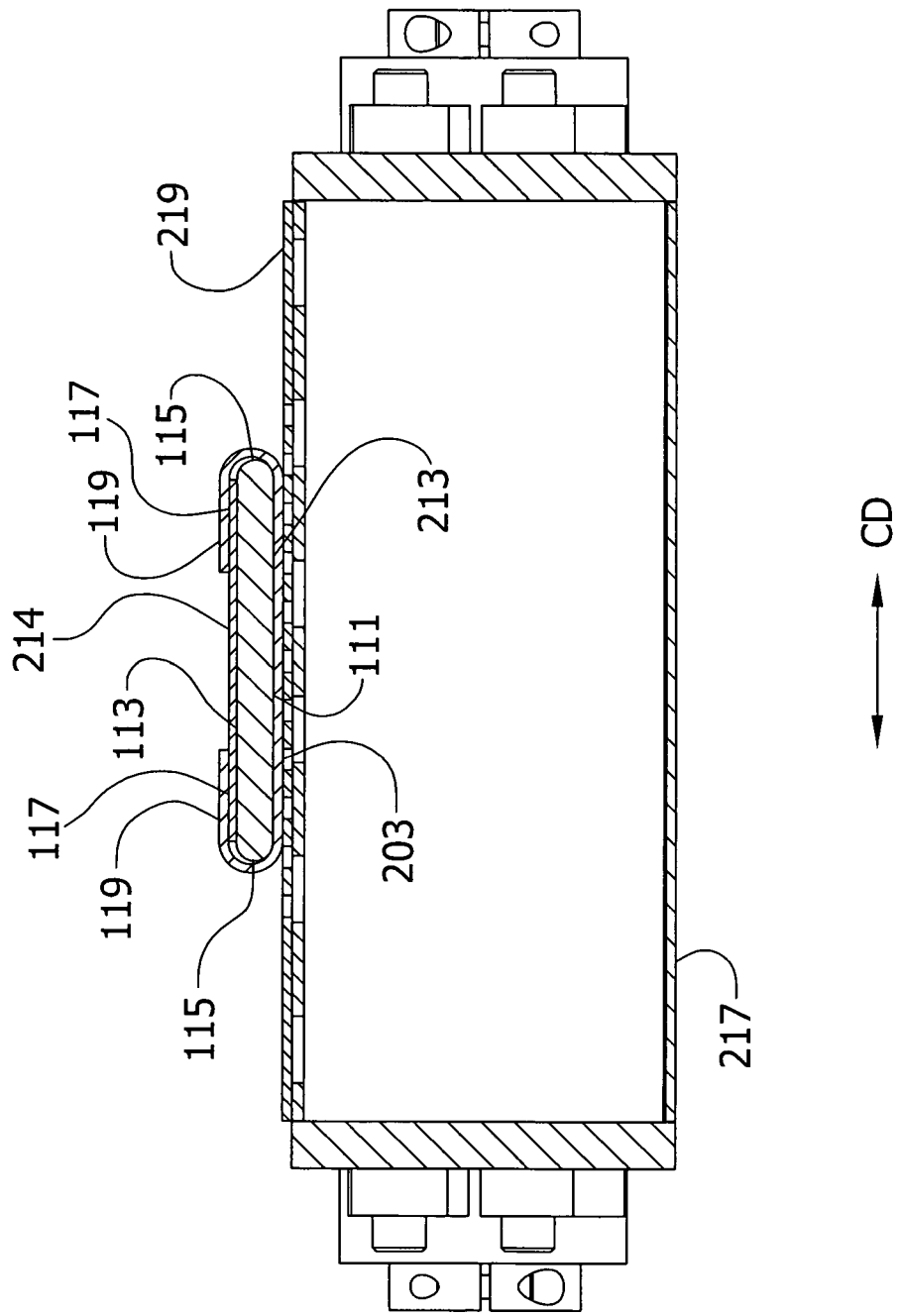
FIG. 16 is a cross-section taken in the plane of line 16-16 of FIG. 11.

Upon exiting the second vacuum unit 229, as shown in FIG. 16, the side margins 119 of the wrapsheet web 203 are wrapped about the side edges 115 of the absorbent core web 213 and are angled inward over the lateral side margins 117 of the cover layer web 214. Suction from the vacuum box 217 draws the wrapsheet web side margins 119 down towards the absorbent core web 213, against the cover layer web 214, as shown in FIGS. 11 and 16, as the wrapsheet web 203 and absorbent core web are conveyed downstream of the second vacuum unit 229. It is also contemplated that a ski (not shown) or other suitable urging member (not shown) may be disposed downstream of the second vacuum unit, and may even be attached to and extend downstream of the second vacuum unit 229, to urge the wrapsheet web side margins 119 down towards the absorbent core web 213, against the cover layer web 214, as the wrapsheet web 203 and absorbent core web are conveyed downstream of the second vacuum unit.

With reference back to FIG. 10, the wrapsheet web 203 and wrapped absorbent core web 213 are drawn from the conveying apparatus 215 by a bonding apparatus 285, such as a conventional debulking apparatus, whereat the wrapsheet web is secured in its wrapped configuration about the absorbent core web, e.g., in the manner described previously herein and shown in FIGS. 3-9 to form a completed absorbent structure web 101. The absorbent structure web 101 is then further processed in a conventional manner to cut the web into discrete absorbent structures for subsequent incorporation into a disposable absorbent article. It is contemplated that the conveying apparatus 215, or other suitable conveying apparatus (not shown) may instead be used to convey the absorbent structure web 101 to the bonding apparatus 285 without departing from the scope of this invention.

The wrapping apparatus 225 shown in FIGS. 10-16 and described above comprises first and second vacuum units 227, 229, with the vacuum slots 249, 279 of the sequentially disposed vacuum units being angled increasingly laterally inward from the first vacuum unit to the second vacuum unit. It is understood that more than two vacuum units may be used to wrap the wrapsheet web 203 about the absorbent core web 213 without departing from the scope of this invention, as long as the vacuum slots are angled increasingly laterally inward from the upstream-most vacuum unit to the downstream-most vacuum unit in the machine direction.

Also, the apparatus 225 shown in FIGS. 11-16 wraps the wrapsheet web 203 about the absorbent core web 213 with the webs in a bodyside-face down configuration. That is, the face of the absorbent core web 203 that faces down against the foraminous belt 219 as the wrapsheet and core webs are moved past the wrapping apparatus 225 corresponds to what becomes the bodyside face 111 (FIG. 5) of the wrapped absorbent core 91 upon incorporation of the wrapped absorbent core into an absorbent article. It is contemplated, however, that the absorbent core web 213 may be wrapped by the wrapsheet web with the bodyside face up, e.g., whereby the wrapsheet web side margins 119 are wrapped down and around the side edges of the absorbent core web 203, without departing from the scope of this invention.

As an example, FIGS. 17-23 illustrate a second embodiment of wrapping apparatus, generally indicated at 325, of the present invention. A web 303 of wrapsheet material, an underlying web 313 of absorbent core material, and a web 314 of cover layer material underlying the absorbent core web are moved through the wrapping apparatus 325 in the machine direction (MD). The wrapsheet web 303, absorbent core web 313 and cover layer web 314 may be brought together in substantially the same manner as described previously and shown in FIG. 10, with the exception that the cover layer web is instead fed to the conveying apparatus 205 upstream of the absorbent core web making apparatus 211 and the wrapsheet material web is fed to the conveying apparatus downstream of the absorbent core web making apparatus. In such an embodiment, the cover layer web 314 and absorbent core web 313 are supported by the conveying apparatus 205 while the wrapsheet web 303 is fed to the conveying apparatus to overlay the absorbent core web with the absorbent core web laterally centrally positioned beneath the wrapsheet web. It is understood that the cover layer web 314, absorbent core web 313 and overlying wrapsheet web 303 may be formed and placed in overlaid relationship in a manner other than as described above without departing from the scope of this invention, as long as the cover layer web, absorbent core web and wrapsheet web are moved through the wrapping apparatus with the cover layer web disposed beneath the absorbent core web and the absorbent core web disposed beneath the wrapsheet web.

Figure 17:
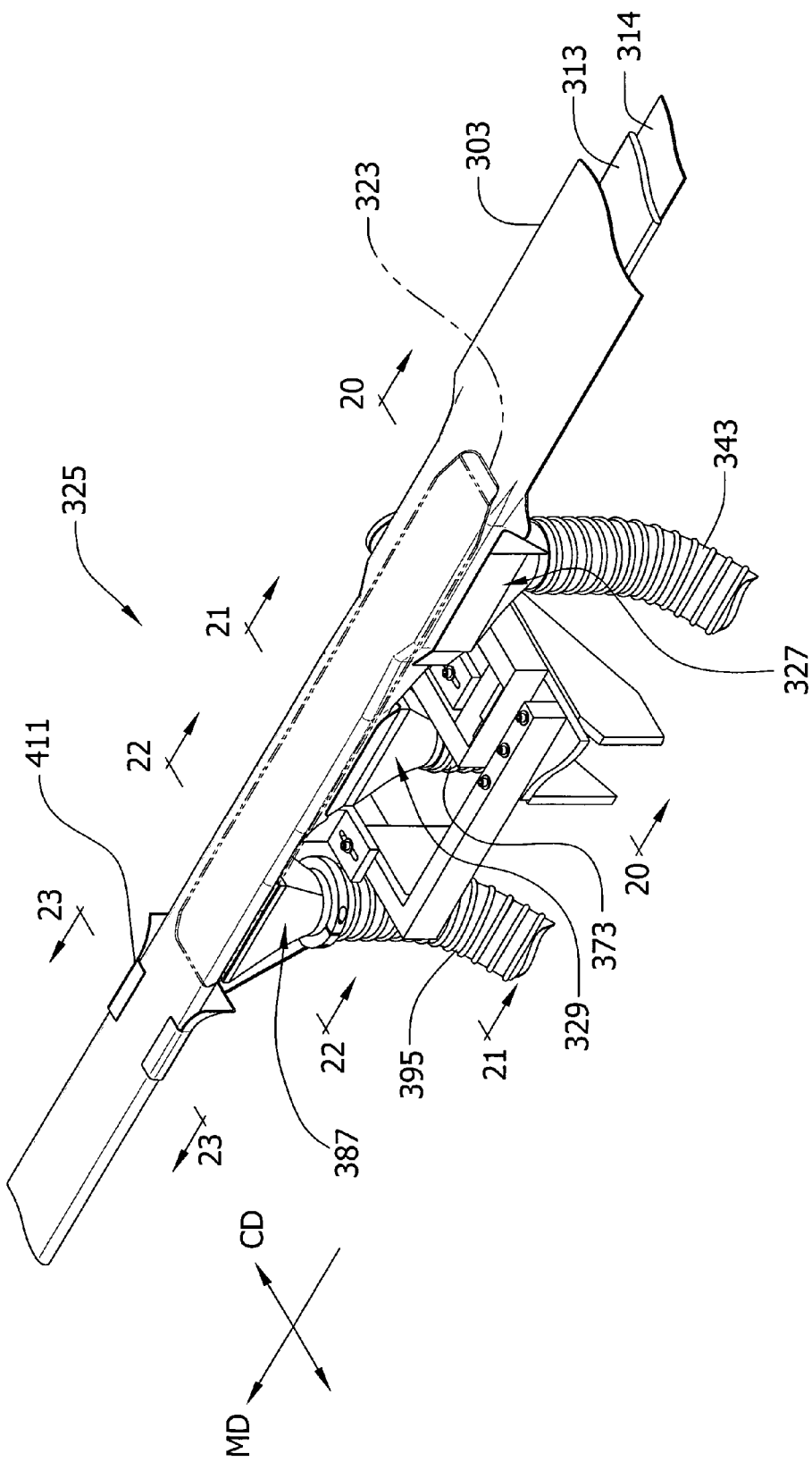
FIG. 17 is a perspective of a second embodiment of wrapping apparatus of the present invention.
Figure 18:
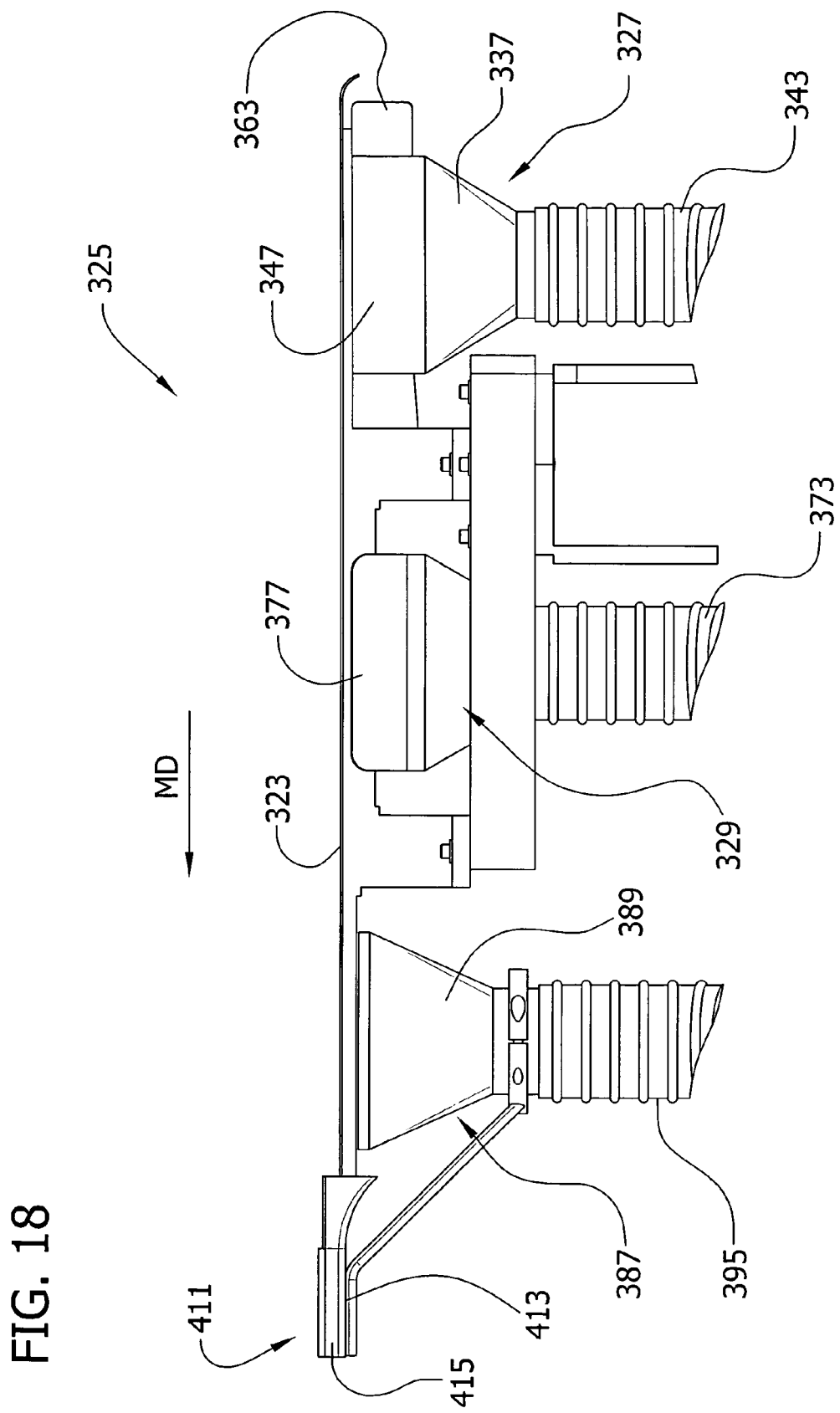
FIG. 18 is a side elevation of the wrapping apparatus of FIG. 17, with the wrapsheet, absorbent core and cover layer omitted.
Figure 19:
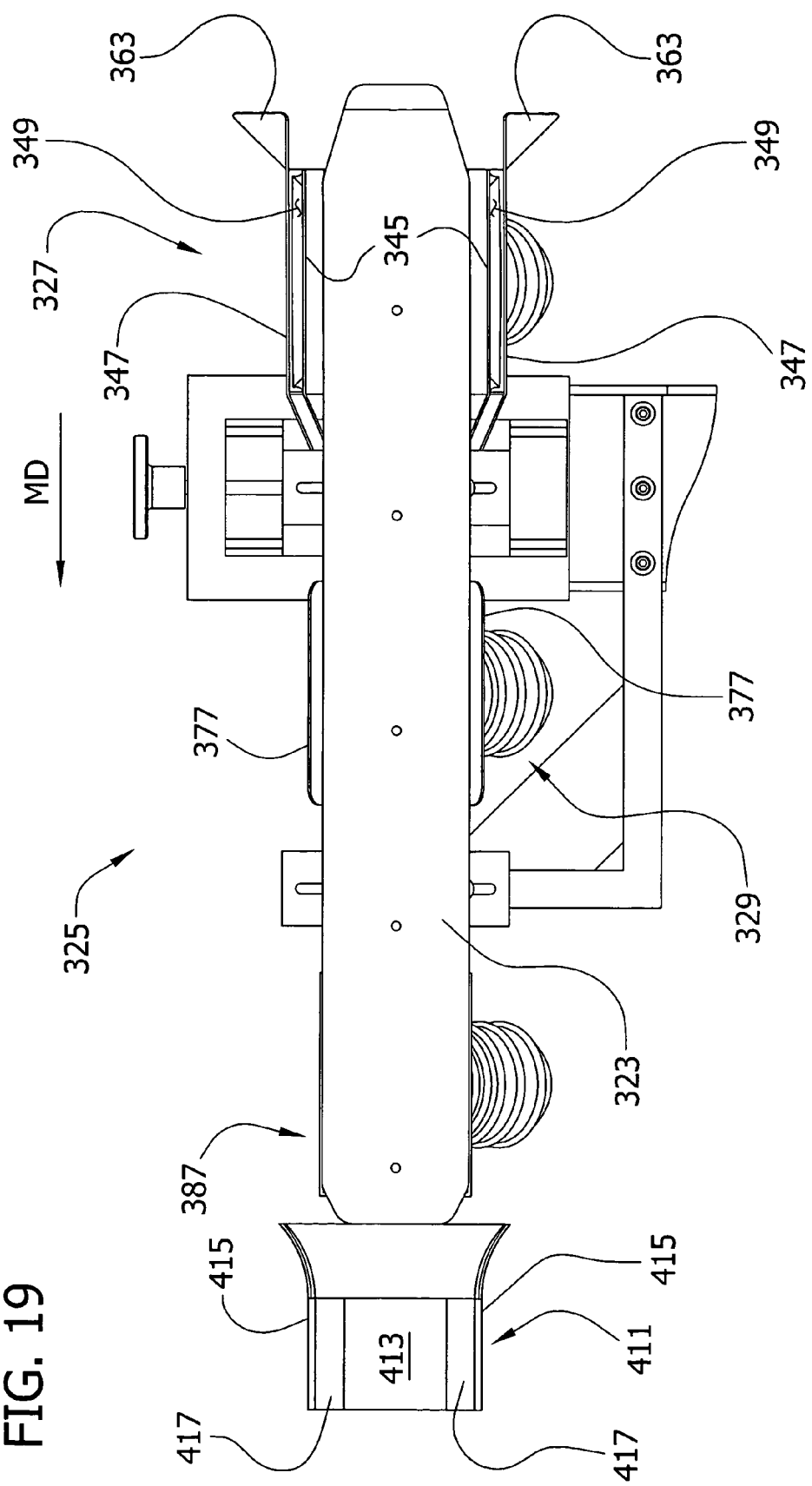
FIG. 19 is a top plan view of the wrapping apparatus of FIG. 17, with the wrapsheet, absorbent core and cover layer omitted.

In the illustrated embodiment of FIG. 17, the wrapsheet web 303, absorbent core web 313 and cover layer web 314 are drawn together past the wrapping apparatus 325 by a bonding device, such as the debulking apparatus 285 of FIG. 10. Thus, the conveying apparatus 215 illustrated in FIGS. 11-16 and described above in connection with the wrapping apparatus 225 of the first embodiment may be omitted from this second embodiment. Alternatively, the web assembly may be conveyed past the wrapping apparatus 325 by a suitable conveyor (not shown) or other apparatus (not shown) without departing from the scope of this invention. The wrapping apparatus 325 of this second embodiment generally comprises an elongate support plate 323 extending in the machine direction of the moving webs 303, 313, 314, with the cover layer web sliding over the plate in contact therewith so as to support the absorbent core web and wrapsheet web as the webs are moved past the wrapping apparatus. The support plate 323 suitably has a width in the range of about 80 percent to about 100 percent of the maximum width of the absorbent core web 313 so that the support plate side edges do not inhibit wrapping of the wrapsheet tight against the side edges of the absorbent core web but otherwise inhibit the absorbent core web side edges 115 against being folded along with the wrapsheet web.

Three vacuum units 327, 329, 387 are disposed below the support plate 323 in sequentially spaced relationship with each other in the machine direction of the moving webs 303, 313, 314. The first vacuum unit 327 is constructed substantially the same as the first vacuum unit 227 of the wrapping apparatus 225 of FIGS. 11-16, including (as seen best in FIGS. 18 and 20) a housing section 337, vacuum inlet 341, conduit 343, and inner and outer fins 345, 347 defining vacuum slots 349 oriented generally perpendicular to the support plate 323 (e.g., to the absorbent core web 313). However, in this embodiment, the first vacuum unit 327 is inverted so that the inner and outer fins 345, 347 (and hence the vacuum slots 349 defined therebetween) extend up from the housing section 337. The inner and outer fins 345, 347 are angled laterally inward toward each other at the downstream portion thereof, such as in the manner of the inner and outer fins 245, 247 of the first vacuum unit 227 of the wrapping apparatus 225 of FIGS. 11-16. The outer fins 347 also comprise guide members 363 angled laterally outward from and canted outward relative to the upstream ends of the outer fins for guiding air flow into the vacuum slots over the surfaces of the guide members to initiate folding of the wrapsheet web side margins 119 while minimizing or inhibiting contact of the wrapsheet web side margins with the guide members. The vacuum slot 349 width, lateral spacing between the inner fins 345, spacing of the fins 345, 347 below the support plate 323, and vacuum pressure for the first vacuum unit 327 may be substantially the same as described above for the wrapping apparatus 225 of the first embodiment.

The second vacuum unit 329 is substantially similar to the second vacuum unit 229 of the wrapping apparatus 225 shown in FIGS. 11-16. Inner and outer fins 375, 377 (FIG. 21) of the second vacuum unit 329 are suitably angled laterally outward from the opposite sides of the housing section 367 at an angle of about 67.5 degrees relative to the machine direction/cross-machine direction plane of the support plate (e.g., of the absorbent core web 313). As with the first vacuum unit 327, the second vacuum unit 329 of the wrapping apparatus 325 of this second embodiment is inverted so that the inner and outer fins 375, 377 (and hence the vacuum slots 379 defined therebetween) extend generally upward instead of downward.

The third vacuum unit 387 is disposed downstream of the second vacuum unit 329, in the machine direction MD, and comprises (with particular reference to FIGS. 18 and 22) a housing section 389, interior vacuum chamber 391, vacuum inlet 393 and vacuum conduit 395 similar to the first and second vacuum units 327, 329. The vacuum pressure provided by the third vacuum unit 387 is suitably in the range of about 5.1 cm (about 2 inches) to about 38.1 cm (about 15 inches) of water, more suitably about 5.1 cm to about 22.9 cm (about 9 inches), and even more suitably about 5.1 cm to about 18 cm (about 7 inches). In general, a lower vacuum pressure and higher airflow is preferred over a higher vacuum pressure and lower airflow. It is also contemplated that the vacuum pressure of the third vacuum unit 387 may be greater or less than the vacuum pressure of the first and/or second vacuum units 327, 329 and remain within the scope of this invention.

Inner fins 397 extend laterally inward toward each other from opposite sides of the housing section 389, i.e., generally parallel to the absorbent core web 313, in spaced relationship with the support plate 323. As an example, the inner fins 397 may suitably spaced below the support plate a distance in the range of about 0.125 to about 2 inches (about 3 to about 51 mm), more suitably 0.125 inches to about 1 inch (about 3 to about 25 mm), even more suitably about 0.25 inches to about 1 inch (about 6 to about 25 mm), and still more suitably about 0.5 inches (about 13 mm). In such a configuration, the support plate 323 and inner fins 397 together define vacuum slots 401 of the third vacuum unit extending generally parallel to the support plate (e.g., to the absorbent core web 313).

With reference to FIGS. 17-23, as the wrapsheet web 303, absorbent core web 313 and underlying cover layer web 314 are drawn past the wrapping apparatus 325, the cover layer web slides on the support plate 323 in the machine direction MD thereof, with the lateral side margins 119 of the wrapsheet web 303 extending laterally outward beyond the side edges of the absorbent core web. Air is drawn by the first vacuum unit 327 over the guide members toward the vacuum slots 349. As the web assembly approaches the first vacuum unit 327, the lateral side margins 119 of the wrapsheet web follow the air flow over the guide members 363 and are raised slightly off of the guide members (e.g., by the air flow) so that the side margins start to fold downward toward the angular orientation of the vacuum slots 349. Upon entering the vacuum slots 349, the side margins 119 of the wrapsheet web 303 are drawn down into the slots so that the side margins of the wrapsheet web become oriented generally perpendicular to the absorbent core web 313 along the opposite side edges of the absorbent core web.

Figure 20:
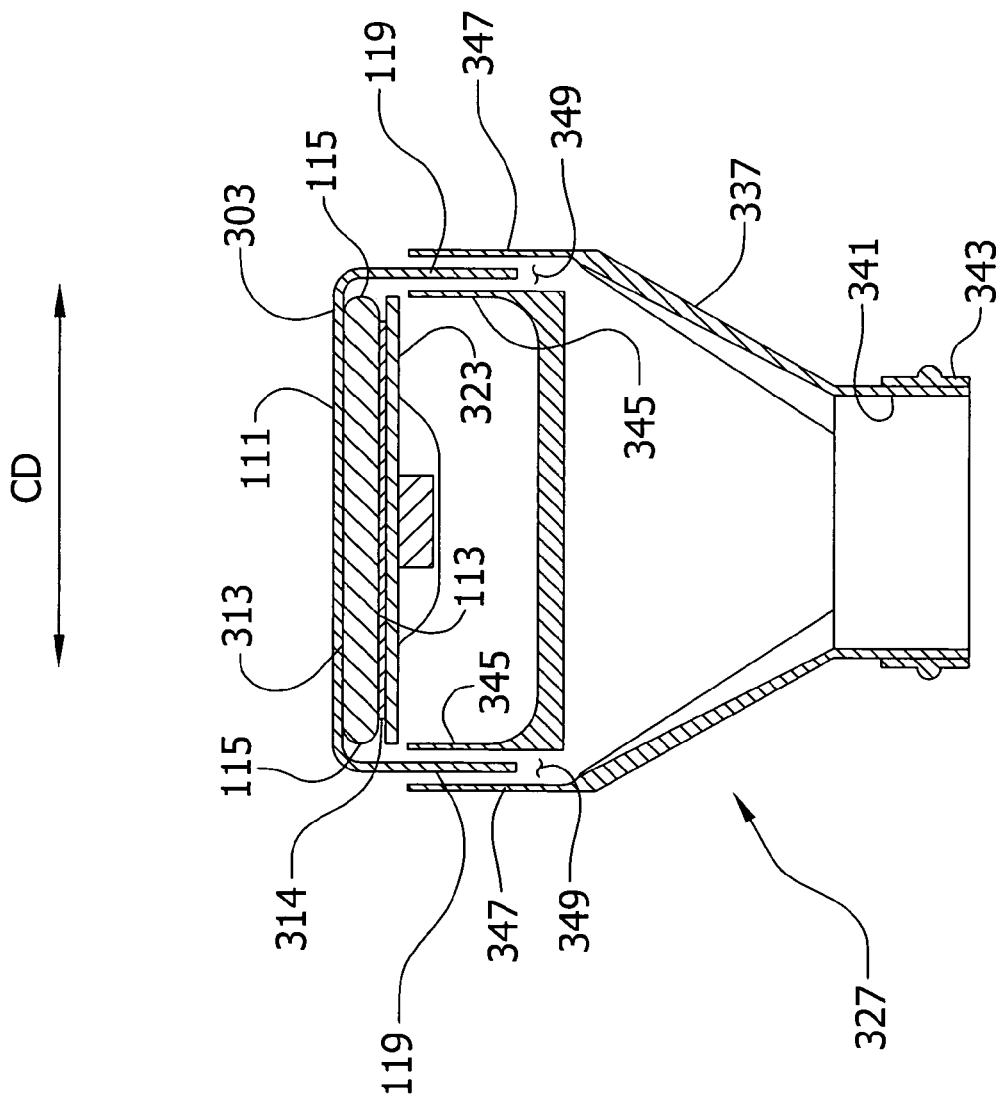
FIG. 20 is a cross-section taken in the plane of line 20-20 of FIG. 17, with portions of the apparatus upstream of line 20-20 omitted.

FIG. 20 is a cross-section taken transversely through the first vacuum unit 327 and illustrates the wrapsheet web side margins 119 being drawn taut and pulled down into the vacuum slots 349. Air is drawn into the slots 349 and flows over both faces of the wrapsheet web side margins 119 to inhibit the side margins of the wrapsheet web against contact with the inner and outer fins 345, 347 that define the vacuum slots. Pulling the wrapsheet web side margins 119 taut in this manner reduces and inhibits wrinkles in the wrapsheet and facilitates a tight wrapping of the wrapsheet web 303 about the absorbent core web 313.

As the wrapsheet web 303 approaches the downstream portion of the fins 345, 347, the wrapsheet web side margins 119 are directed generally laterally inward by the laterally inward angled orientation of the downstream portion of the inner and outer fins. Directing the wrapsheet web side margins 119 laterally inward in this manner is intended to more closely align the lateral (e.g., cross-machine direction) position of the wrapsheet web side margins with the upstream end of the inner and outer fins 375, 377 of the second vacuum unit 329. Upon entering the vacuum slots 379 defined by the inner and outer fins 375, 377 of the second vacuum unit 329, the side margins 119 of the wrapsheet web 303 are drawn into the vacuum slots and pulled taut at a more laterally inward directed angular orientation relative to the absorbent core web 313 and support plate 323.

Figure 21:
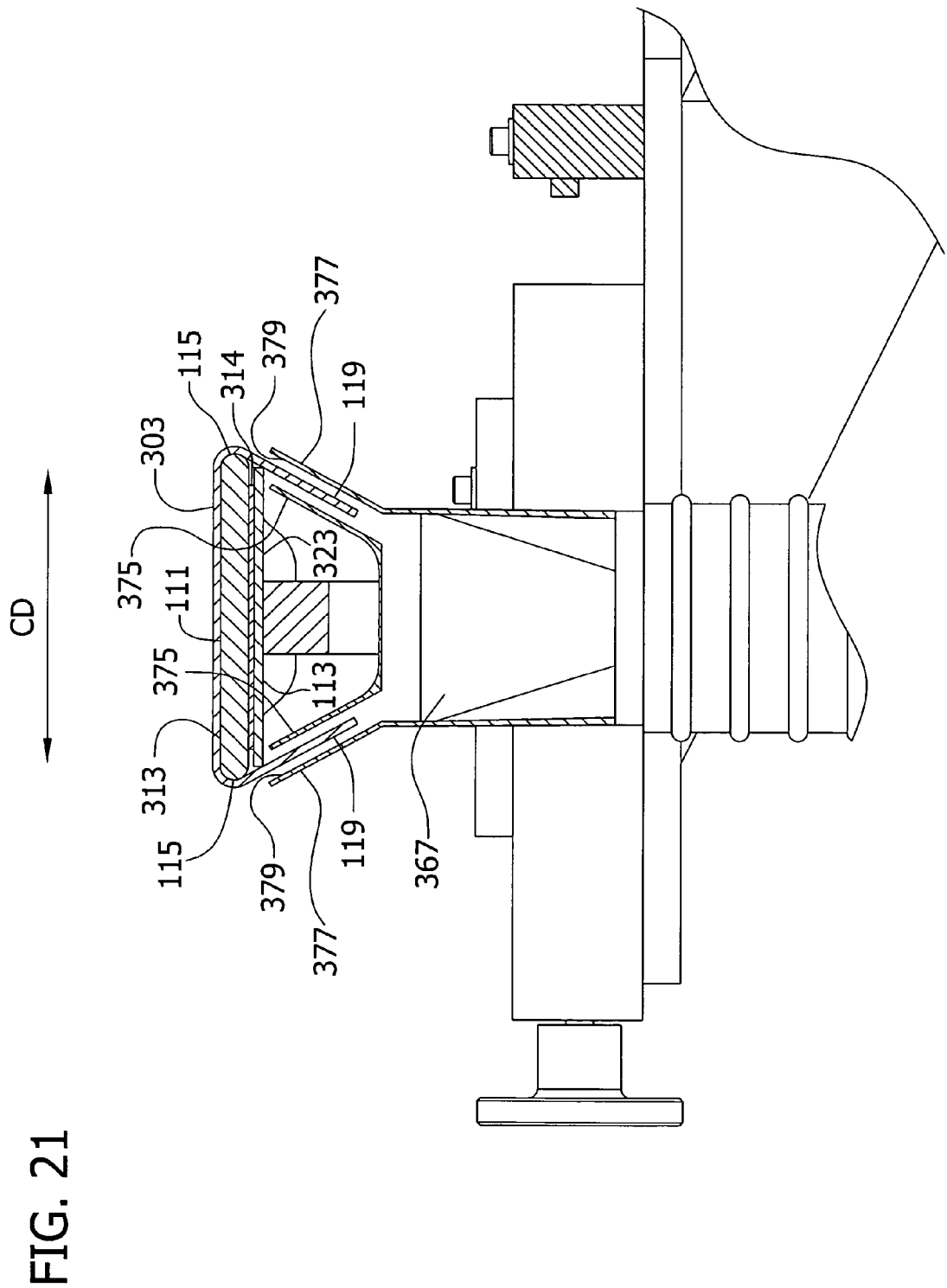
FIG. 21 is a cross-section taken in the plane of line 21-21 of FIG. 17, with portions of the apparatus upstream of line 21-21 omitted.

FIG. 21 is a cross-section taken transversely through the second vacuum unit 329 and illustrates the further inward pulling of the wrapsheet web side margins 119 by the second vacuum unit. As in the first vacuum unit 327, air is drawn into the slots 379 of the second vacuum unit 329 and flows over both faces of the wrapsheet web side margins to inhibit the side margins of the wrapsheet web against contact with the inner and outer fins 375, 377. Because the lateral spacing between the inner fins 375 is equal to or less than the maximum width of the absorbent core web 313, the side margins 119 of the wrapsheet web 303 are pulled taut against (i.e., wrapped generally tightly about) the side edges 115 of the absorbent core web (e.g., at those portions of the absorbent core web having a width greater than or equal to the lateral spacing between the inner fins).

Figure 22:
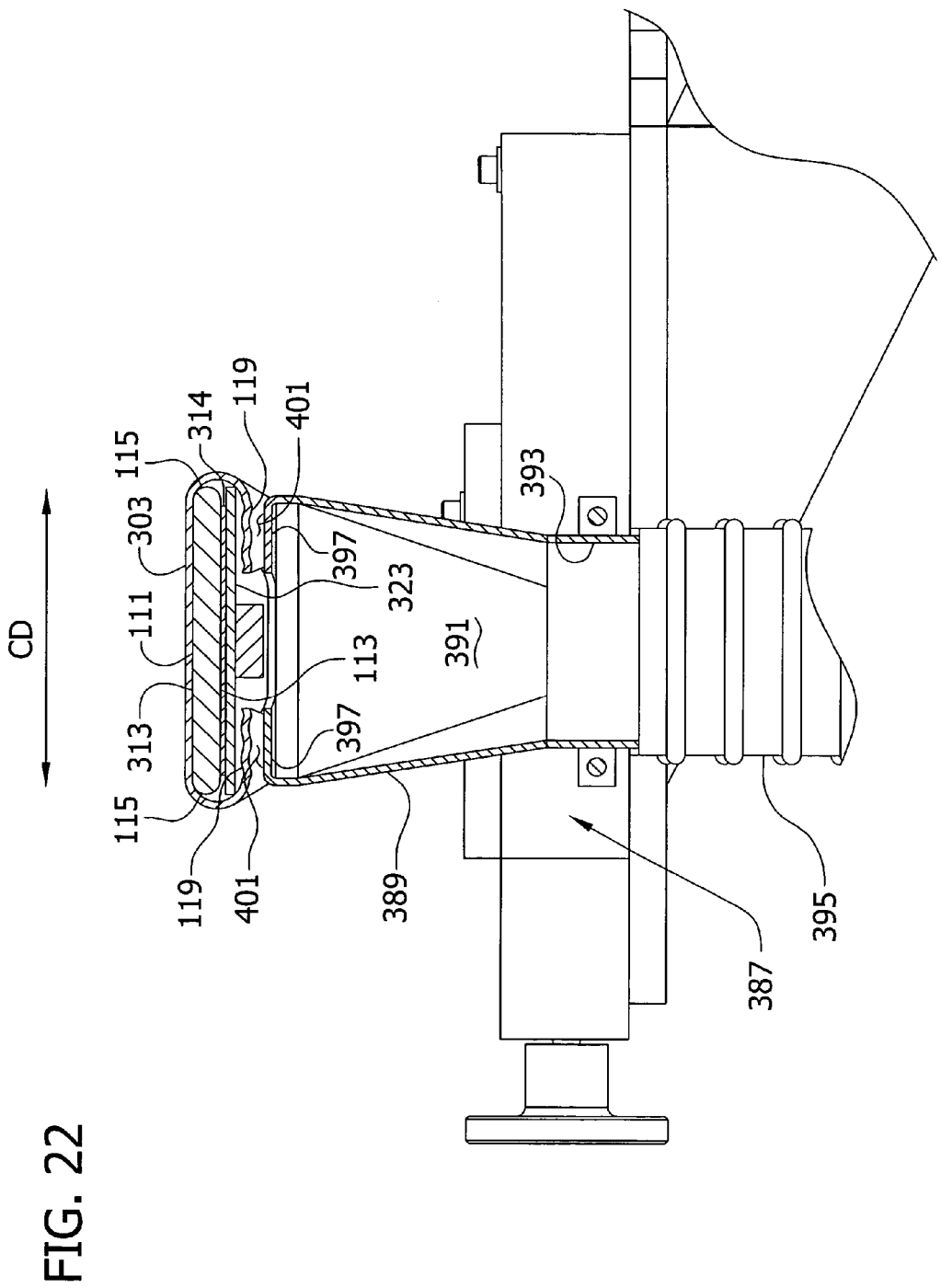
FIG. 22 is a cross-section taken in the plane of line 22-22 of FIG. 17, with portions of the apparatus upstream of line 22-22 omitted.

FIG. 22 is a cross-section taken transversely through the third vacuum unit 387. As the wrapsheet reaches the third vacuum unit 387, vacuum pressure from the vacuum chamber 391 draws air laterally inward between the inner fins 397 and the support plate 323 (e.g., into the vacuum slots 401 defined therebetween) to draw the lateral side margins 119 laterally inward parallel with the support plate, cover layer web 314 and absorbent core web 313.

Figure 23:
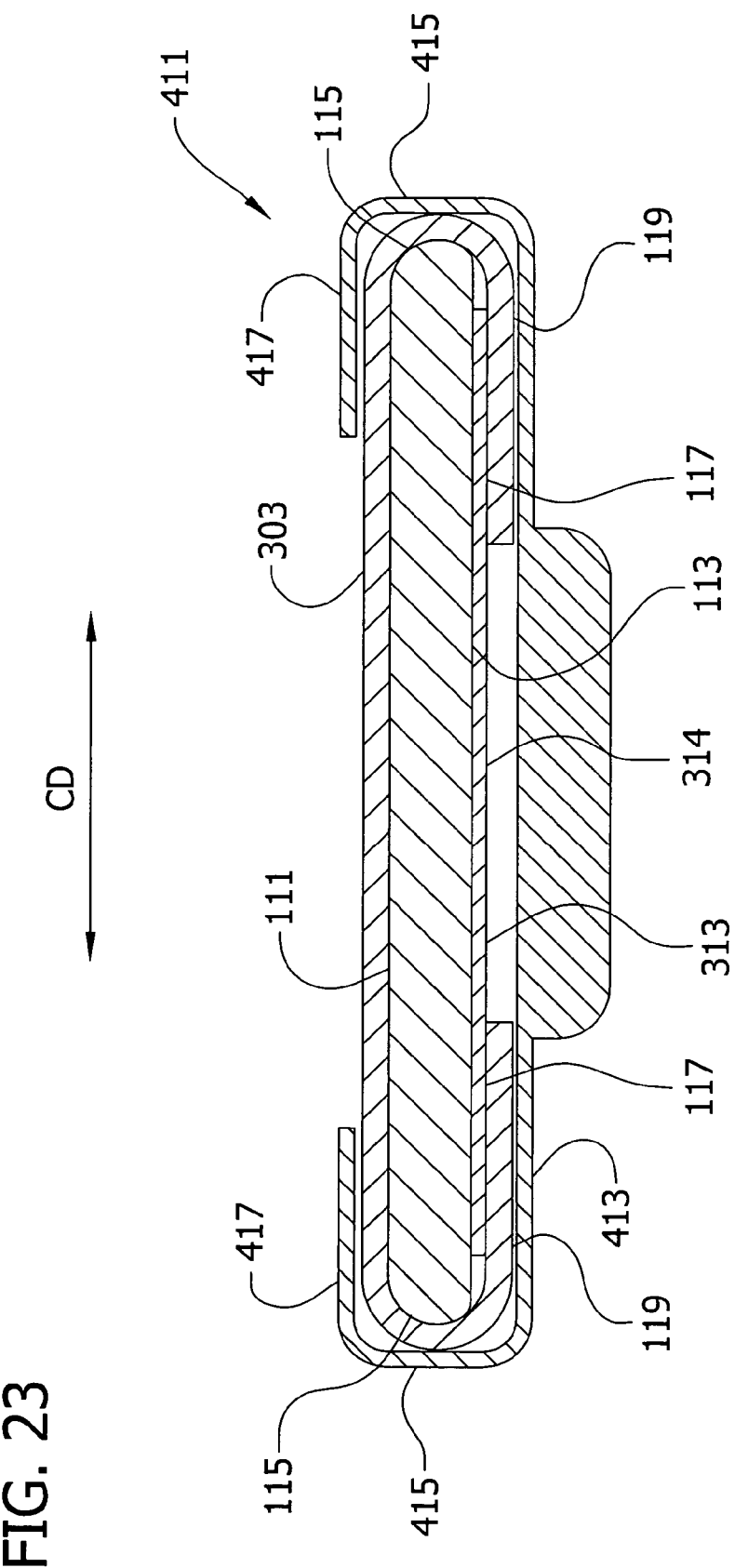
FIG. 23 is a cross-section taken in the plane of line 23-23 of FIG. 17.

Upon moving downstream of the third vacuum unit 387, as shown in FIGS. 17 and 23, the wrapped absorbent core web 313 and cover layer 314 slides off of the support plate 323 and enters a forming member 411. The forming member 411 comprises a bottom plate 413, laterally opposite side walls 415 and opposed, generally L-shaped flange members 417 extending laterally inward from the side walls over the bottom plate. The flange members 417 retain the wrapsheet web 303 in its wrapped configuration about the absorbent core web 313 and cover layer web 314 as the webs are drawn further downstream into the bonding device (e.g., debulking device 285 as shown in FIG. 10) for securement of the wrapsheet web in its wrapped configuration to define the continuous absorbent structure web 101. Alternatively, the web assembly may be conveyed by suitable conveyor (not shown) to the bonding device without departing from the scope of this invention. The absorbent structure web 101 (FIG. 10) is then further processed in a conventional manner to cut the web into discrete absorbent structures for subsequent incorporation into a disposable absorbent article.

The wrapping apparatus shown in FIGS. 17-23 and described above comprises three discrete vacuum units 327, 329, 387, with the vacuum slots 349, 379, 401 of the sequentially disposed vacuum units being angled increasingly laterally inward relative to the absorbent core web 313 from the first vacuum unit to the third vacuum unit. It is understood, however, that more than three vacuum units may be used, or that only two vacuum units may be used, to wrap the wrapsheet web 303 about the absorbent core web 313 without departing from the scope of this invention, as long as the vacuum slots of such vacuum units are angled increasingly laterally inward from the upstream-most vacuum unit to the downstream-most vacuum unit in the machine direction of the webs.

FIGS. 24-29 illustrate a third embodiment of wrapping apparatus, generally indicated at 525, of the present invention in which vacuum pressure is used to draw and retain the side margins 119 of a wrapsheet web 503 in contact with the wrapping apparatus as the side margins are wrapped about an absorbent core web 513 and cover layer web 514. The wrapsheet web 503, absorbent core web 513 and cover layer web 514 may be of the same construction, and constructed in the same manner, as described previously, and more suitably with the cover layer web and absorbent core web overlaid in laterally central position on the wrapsheet web. The cover layer web, absorbent core web 513 and underlying wrapsheet web 503 may be formed and placed in overlaid relationship in the manner described previously and shown in FIG. 10, or in another suitable manner, and remain within the scope of this invention.

Figure 24:
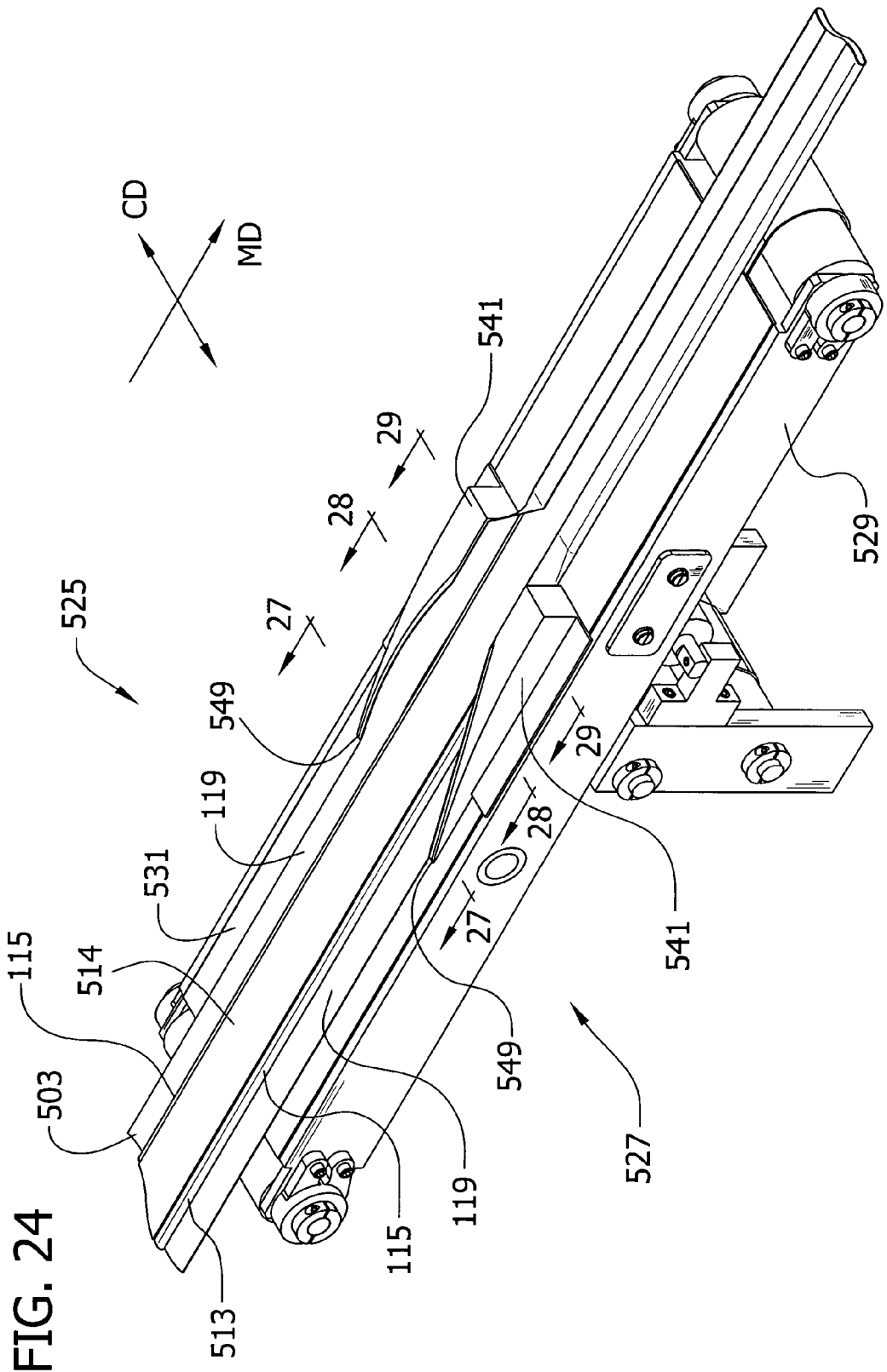
FIG. 24 is a perspective of a third embodiment of wrapping apparatus of the present invention.
Figure 25:
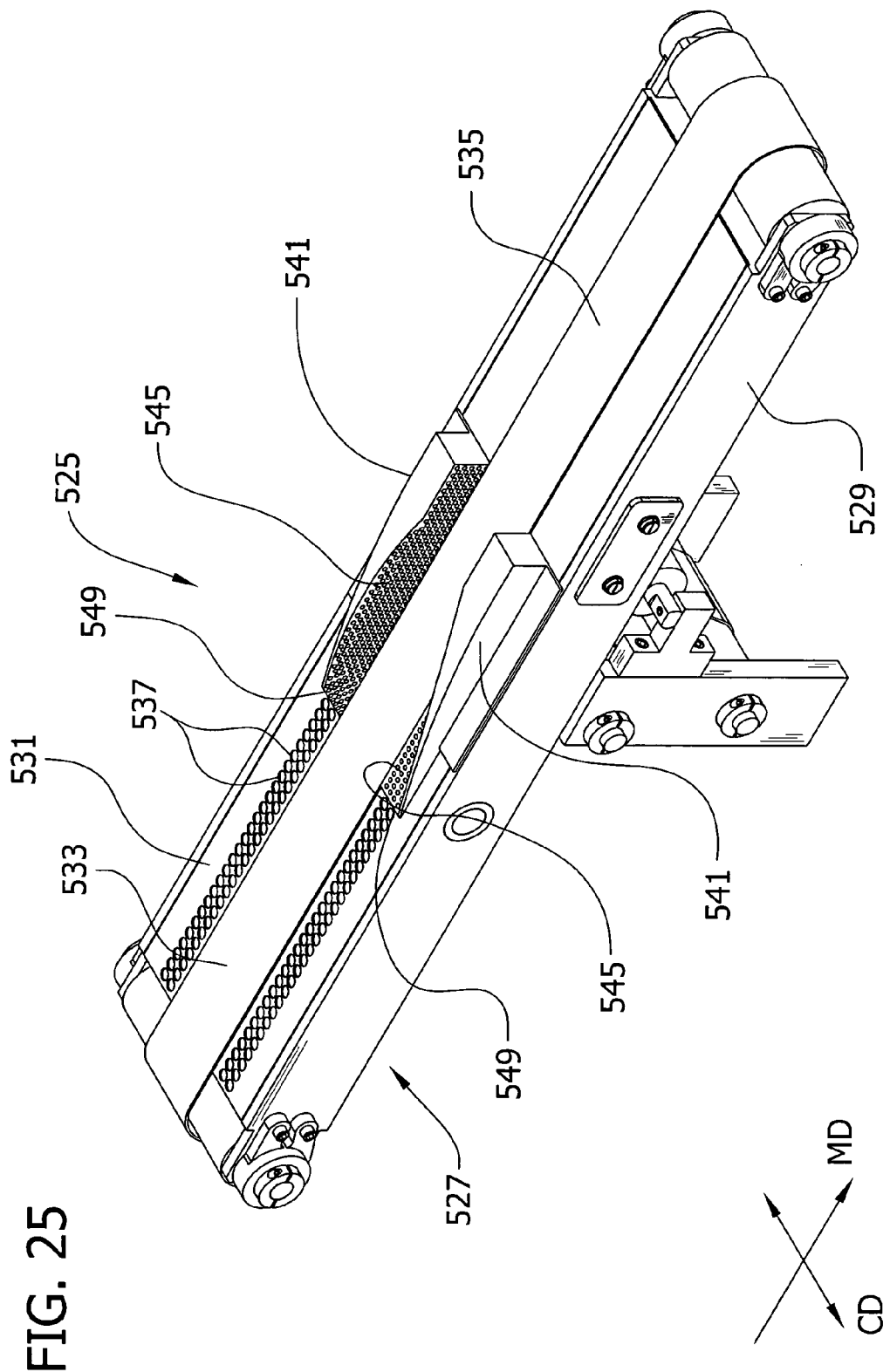
FIG. 25 is a perspective substantially as shown in FIG. 24 but with the wrapsheet, absorbent core and cover layer omitted.
Figure 26:
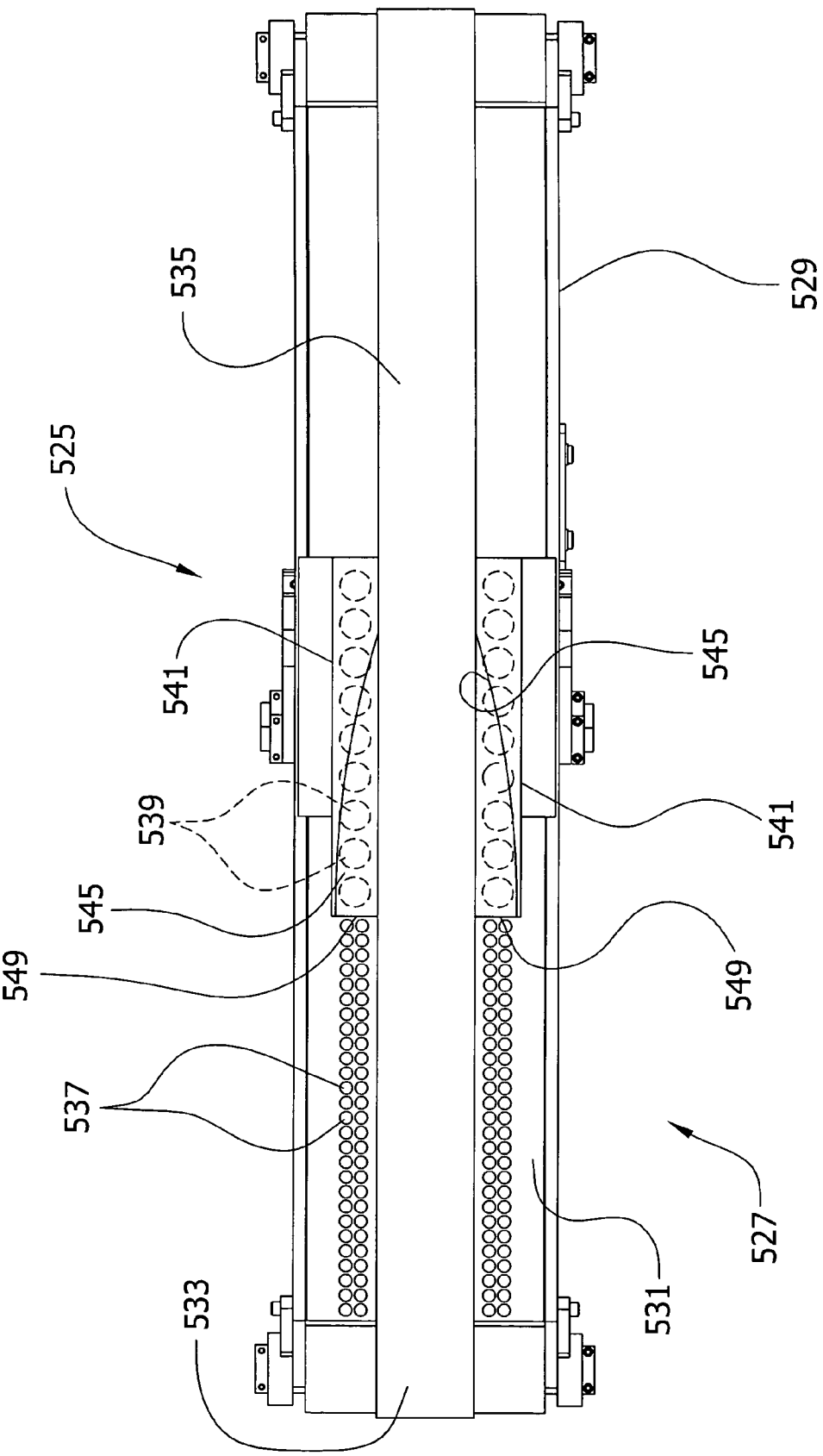
FIG. 26 is a top plan view of the wrapping apparatus of FIG. 25.

With particular reference to FIGS. 24 and 25, the wrapsheet web 503, absorbent core web 513 and cover layer web 514 are conveyed past the wrapping apparatus 525 by conveying apparatus 527 comprised of a vacuum box 529 having a foraminous top plate 531 thereon, and a continuous foraminous belt 533 having an upper reach 535 that moves over the foraminous top plate of the vacuum box in the machine direction and has a width substantially less than the width of the foraminous top plate of the vacuum box. For example, openings 537 in the vacuum box top plate 531 are shown in FIG. 25 as extending laterally out beyond the side edges of the foraminous belt 533 upstream of the wrapping apparatus 525, with larger openings 539 (FIG. 26) being disposed in the top plate 531 laterally outward of the side edges of the belt beneath the wrapping apparatus 525 to provide fluid communication between the wrapping apparatus and the vacuum box 529 for reasons which will become apparent.

The wrapping apparatus 525 of this third embodiment comprises a pair of elongate, laterally opposed skis 541 extending longitudinally in the machine direction (MD) of the moving wrapsheet web 503, absorbent core web 513 and cover layer web 514 and disposed generally adjacent the side edges of the foraminous belt 533. For example, in the illustrated embodiment the skis 541 are mounted on the vacuum box 529 at laterally opposite sides thereof and extend laterally inward from the sides of the vacuum box to the side edges of the foraminous belt 533. Each ski 541 is generally hollow and defines an interior vacuum chamber 543 (FIG. 27) within the ski. The ski 541 is open along its bottom such that the interior chamber 543 of the ski overlays the large openings 539 in the top plate 531 of the vacuum box 529 to provide fluid communication between the vacuum box and the interior chamber of the ski.

Each ski 541 has a foraminous inner side wall 545 that extends along the length of the ski in a generally helical pattern. That is, the inner side wall 545 has a slope in the cross-machine direction that gradually changes in angular orientation from an angle of about 0 degrees relative to the foraminous belt 533 (and hence the absorbent core web 513), i.e., generally parallel thereto, to an angle of about 90 degrees, i.e., perpendicular to the foraminous belt and absorbent core web, as the inner side wall extends along the length of the ski. The inner side wall 545 has a plurality of smaller openings 547 (FIG. 27) formed therein in fluid communication with the interior chamber 543 of the ski 541 to draw air into the interior chamber via the openings in the side wall. As an example, the openings 547 in the inner side wall 545 of each ski 541 are suitably in the range of about 0.625 inches to about 0.75 inches (about 1.6 mm to about 19.1 mm), more suitably in the range of about 0.125 inches to about 0.5 inches (about 3.2 mm to about 12.7 mm), and even more suitably about 0.5 inches (about 12.7 mm). In the illustrated embodiment, the top plate 531 of the vacuum box 529 has-a depression or seat (not shown) formed therein, such as by etching or other suitable technique, generally beneath an upstream end 549 of each ski 541. The upstream end 549 of the ski 541 seats in the depression with the inner side wall 545 of the ski at its upstream end generally flush with the top plate 531 of the vacuum box 529 to provide a smooth transition from the top plate of the vacuum box to the inner side wall of the ski in the machine direction.

With particular reference to FIGS. 24 and 27-29, in operation the wrapsheet web 503 and overlying absorbent core web 513 and cover layer web 514 are conveyed by the conveying apparatus 527 to the wrapping apparatus 525, with the side margins 119 of the wrapsheet web (e.g., the wrapsheet web portions that extend laterally outward beyond the side edges 115 of the absorbent core web) drawn down against and slidingly moved over the top plate 531 of the vacuum box 529 laterally outward of the sides of the foraminous belt 533 (e.g., via the openings 537 in the top plate of the vacuum box). At the upstream ends 549 of the skis 541, the foraminous belt 533 carries the absorbent core web 513 and its underlying portion of the wrapsheet web 503 between the skis in the machine direction while the side margins 119 of the wrapsheet web are moved onto the inner side walls 545 of the skis. The wrapsheet web side margins 119 are drawn against and retained on the inner side walls 545 of the skis 541 by vacuum pressure supplied thereto via the small openings 547 in the inner side walls of the skis.

Figure 27:
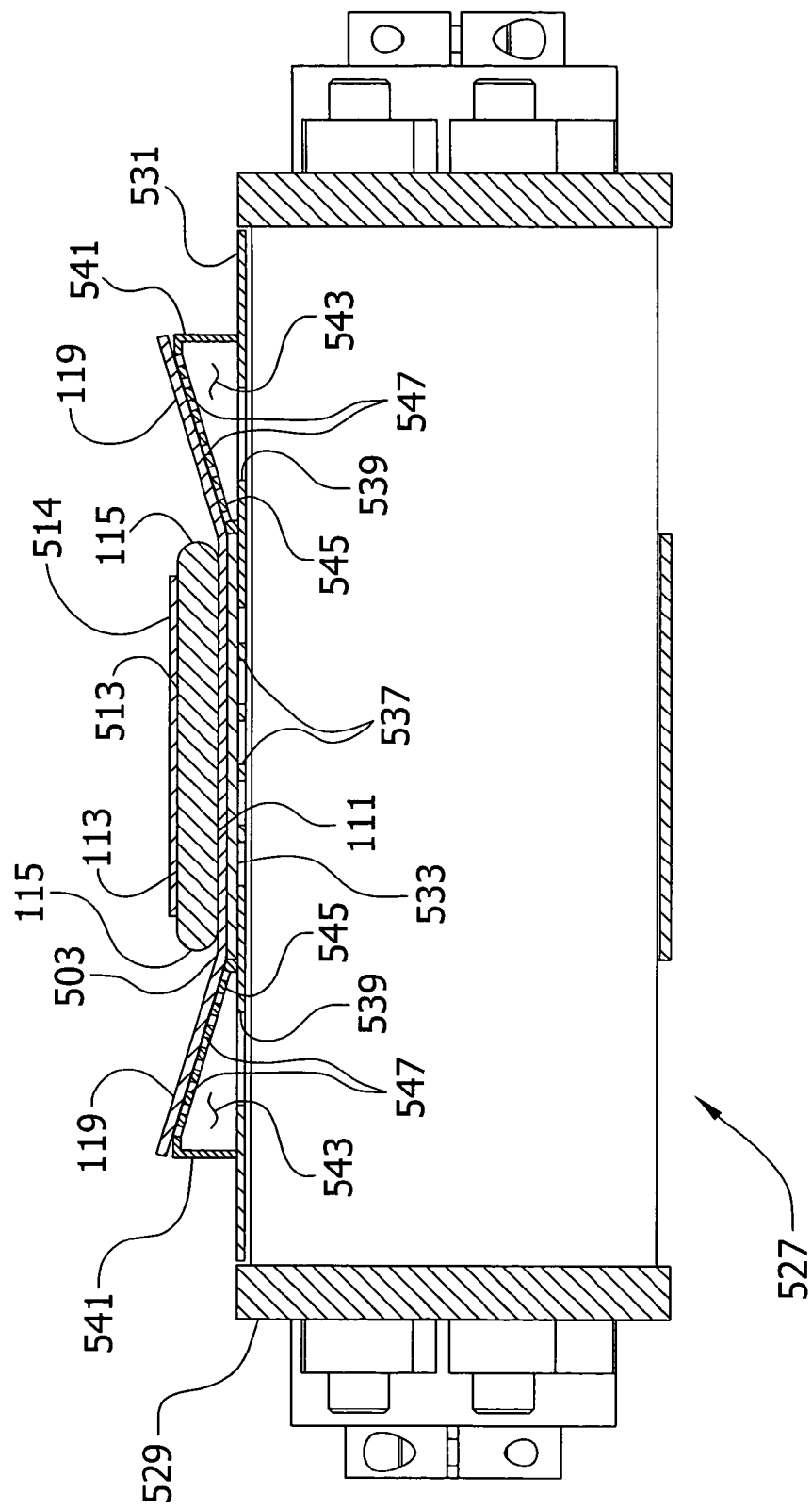
FIG. 27 is a cross-section taken in the plane of line 27-27 of FIG. 24.
Figure 28:
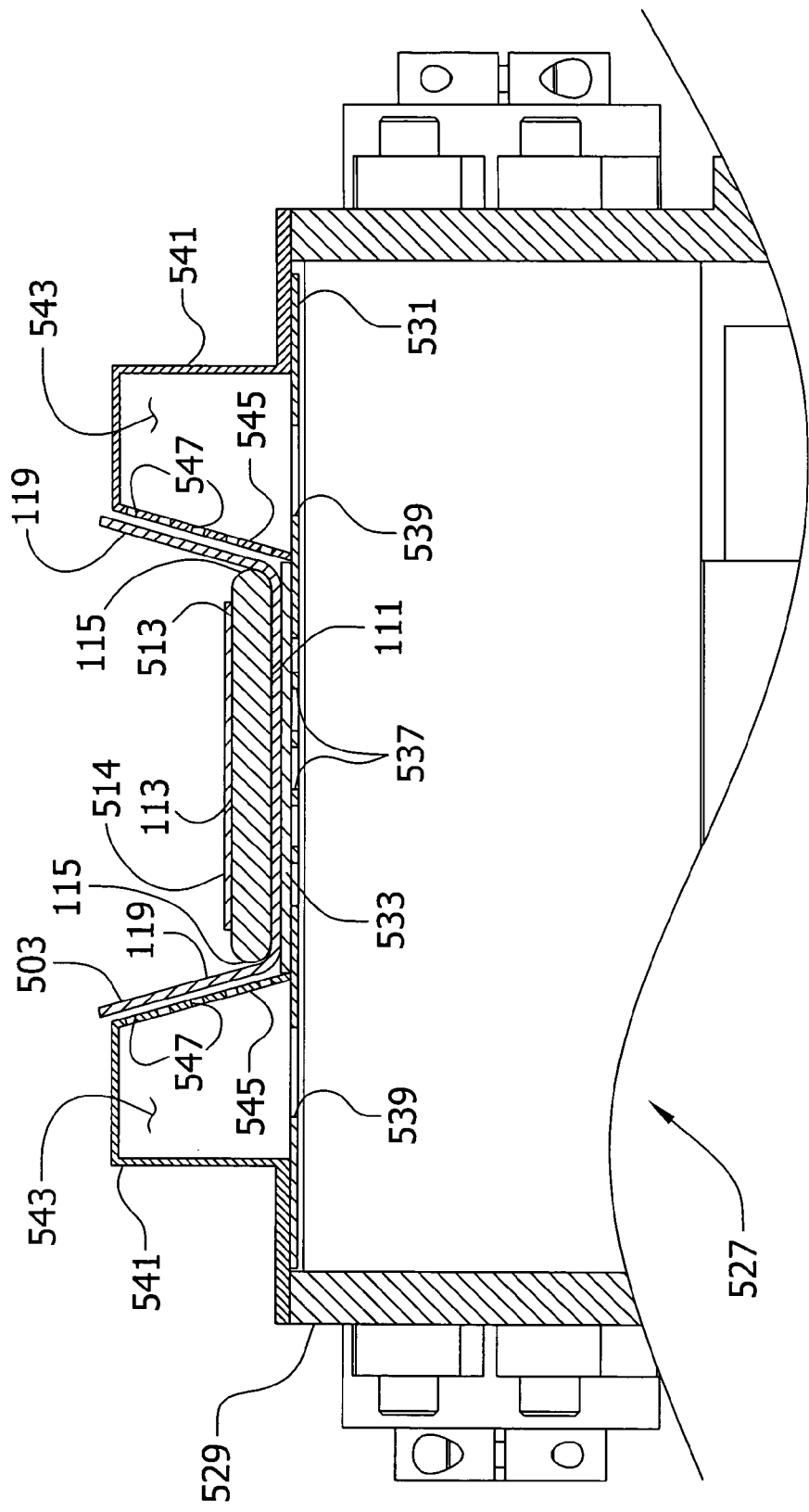
FIG. 28 is a cross-section taken in the plane of line 28-28 of FIG. 24.
Figure 29:
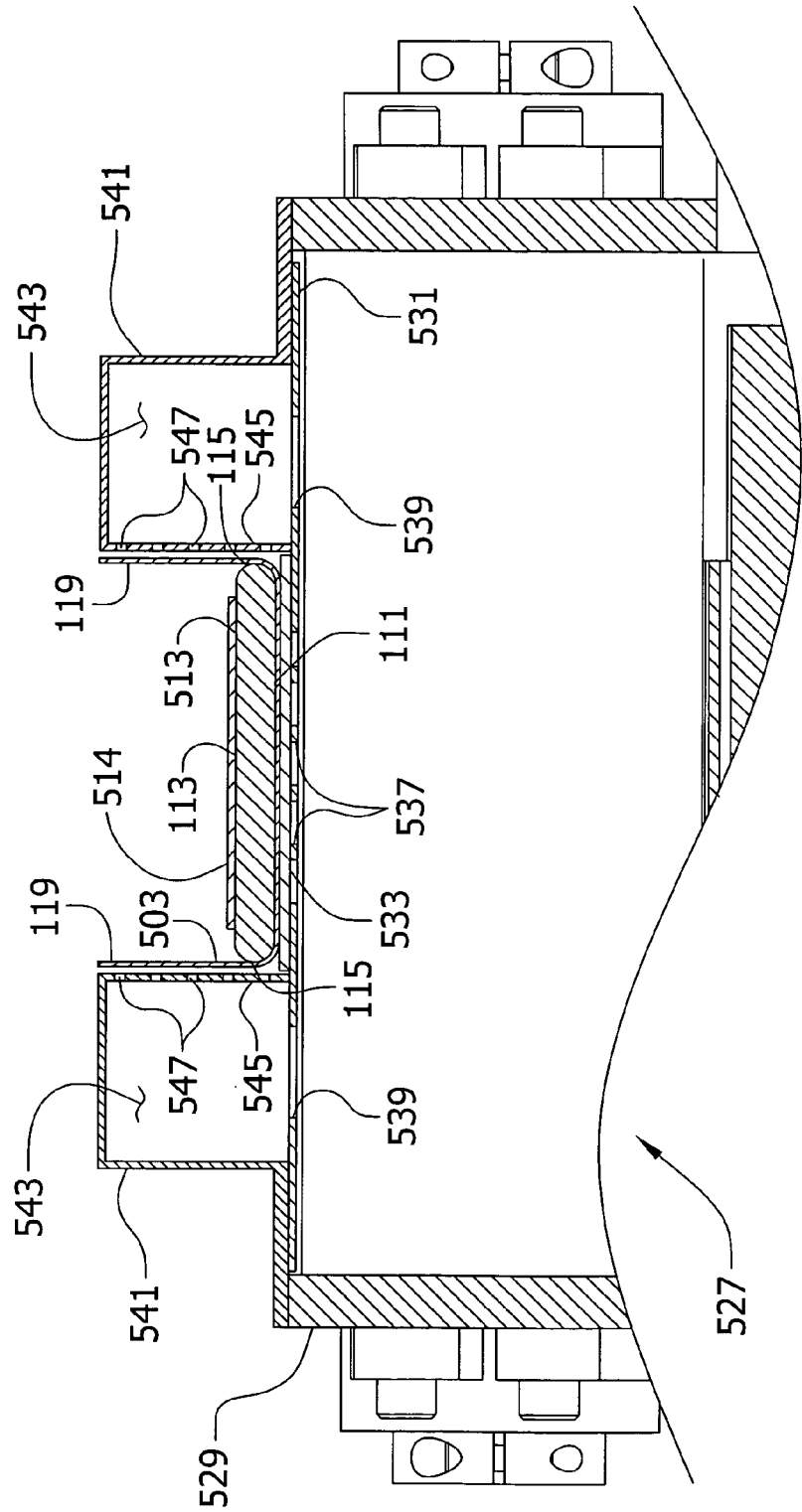
FIG. 29 is a cross-section taken in the plane of line 29-29 of FIG. 24.
Figure 30:
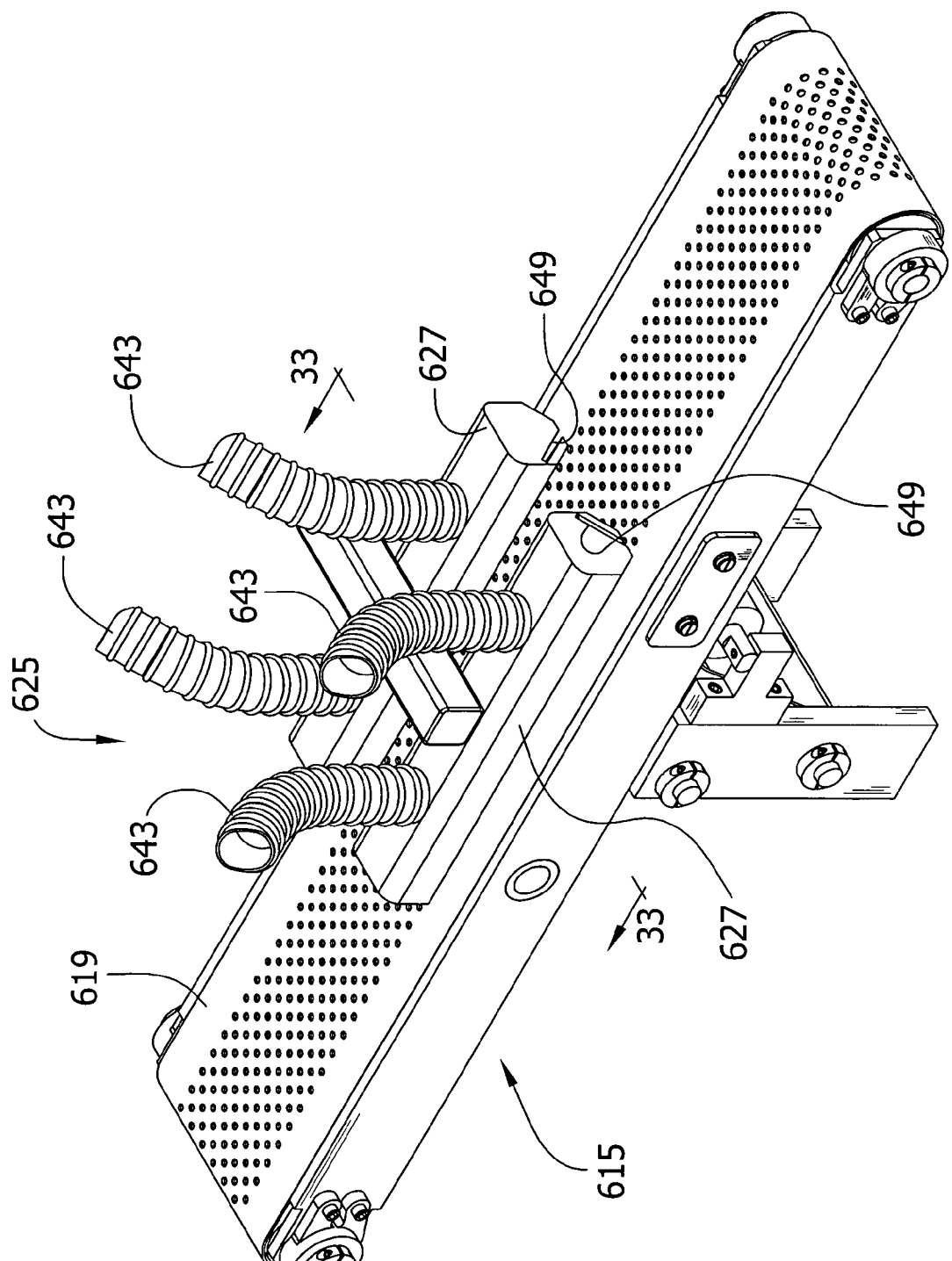
FIG. 30 is a perspective of a fourth embodiment of wrapping apparatus of the present invention.

As each of the wrapsheet web side margins 119 is moved further downstream on the inner side wall 545 of a respective one of the skis 541, the generally helical pattern of the inner side wall changes the orientation of the wrapsheet web side margin to generally wrap the wrapsheet web about the side edges of the absorbent core web 513. For example, FIGS. 27-29 illustrate the orientations of the wrapsheet web side margins 119 at various positions along the lengths of the skis 541. Upon exiting the downstream end of the wrapping apparatus 525, the side margins 119 of the wrapsheet web 503 extend generally perpendicular to the absorbent core web 513 up against the side edges of the absorbent core web. Suction from vacuum box 529 (via the foraminous belt 533) draws the wrapsheet web side margins 119 down towards the absorbent core web and against the lateral side margins 117 of the cover layer web 514 as shown in FIG. 24 as the web assembly is conveyed downstream of the wrapping apparatus 525.

The wrapsheet web 503, wrapped absorbent core web 513 and cover layer web 514 are drawn from the conveying apparatus 527 by a bonding apparatus, such as the conventional debulking apparatus 285 shown in FIG. 10, whereat the wrapsheet web is secured in its wrapped configuration about the absorbent core web, e.g., in the manner described previously herein, to form a continuous absorbent structure web 101. Alternatively, the web assembly may be conveyed, such as by conveying apparatus 527 or other suitable apparatus, to the bonding apparatus without departing from the scope of this invention. The absorbent structure web 101 is then further processed in a conventional manner to cut the web into discrete absorbent structures for subsequent incorporation into a disposable absorbent article.

FIGS. 30-33 illustrate a fourth embodiment similar of wrapping apparatus, generally indicated at 625, that is substantially similar to the wrapping apparatus 225 of FIGS. 11-16 in that the absorbent core web, wrapsheet web and cover layer web (none of which are shown in FIGS. 30-33 but are substantially the same as the webs shown in FIGS. 11-16) are conveyed by suitable conveying apparatus 615 past the wrapping apparatus 625 with the absorbent core web overlaying the wrapsheet web (e.g., so that the side margins of the wrapsheet are wrapped by the wrapping apparatus upward about the absorbent core web). The wrapping apparatus 625 of this fourth embodiment comprises a pair of elongate vacuum units 627 extending longitudinally (e.g., in the machine direction MD) in laterally spaced relationship with each other above a foraminous belt 619 of the conveying apparatus 615. In this configuration, the elongate vacuum units 627 essentially replace the sequentially spaced first and second vacuum units 227, 229 of the wrapping apparatus 225 of FIGS. 11-16. Each of the vacuum units 627 comprises an interior vacuum chamber 639 (FIG. 33) in fluid communication with a vacuum source (not shown) via vacuum conduits 643. A vacuum slot 649 extends longitudinally in each vacuum unit 627 the entire length thereof (e.g., from the upstream end to the downstream end of the vacuum unit) in fluid communication with the interior vacuum chamber of the vacuum unit.

Figure 31:
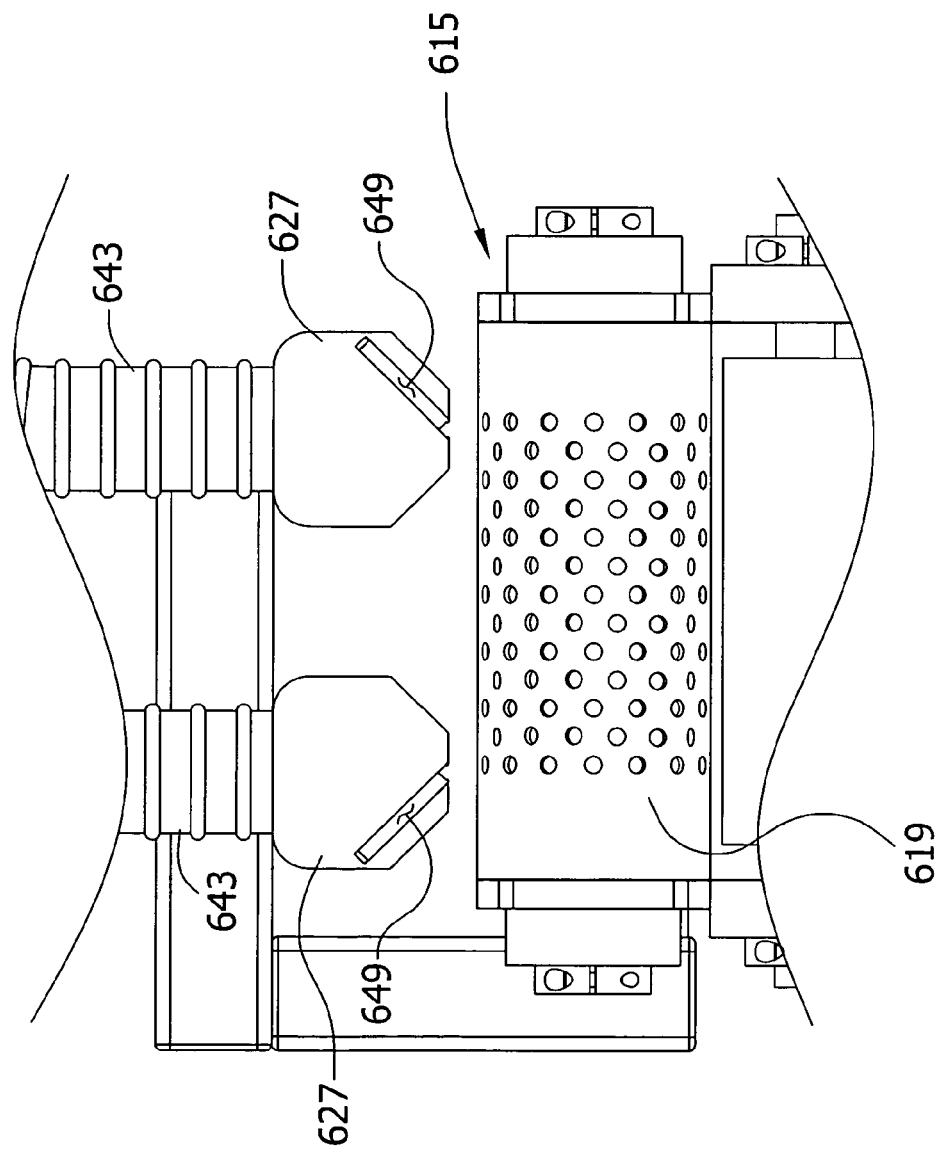
FIG. 31 is a partial front elevation of the wrapping apparatus of FIG. 30.
Figure 32:
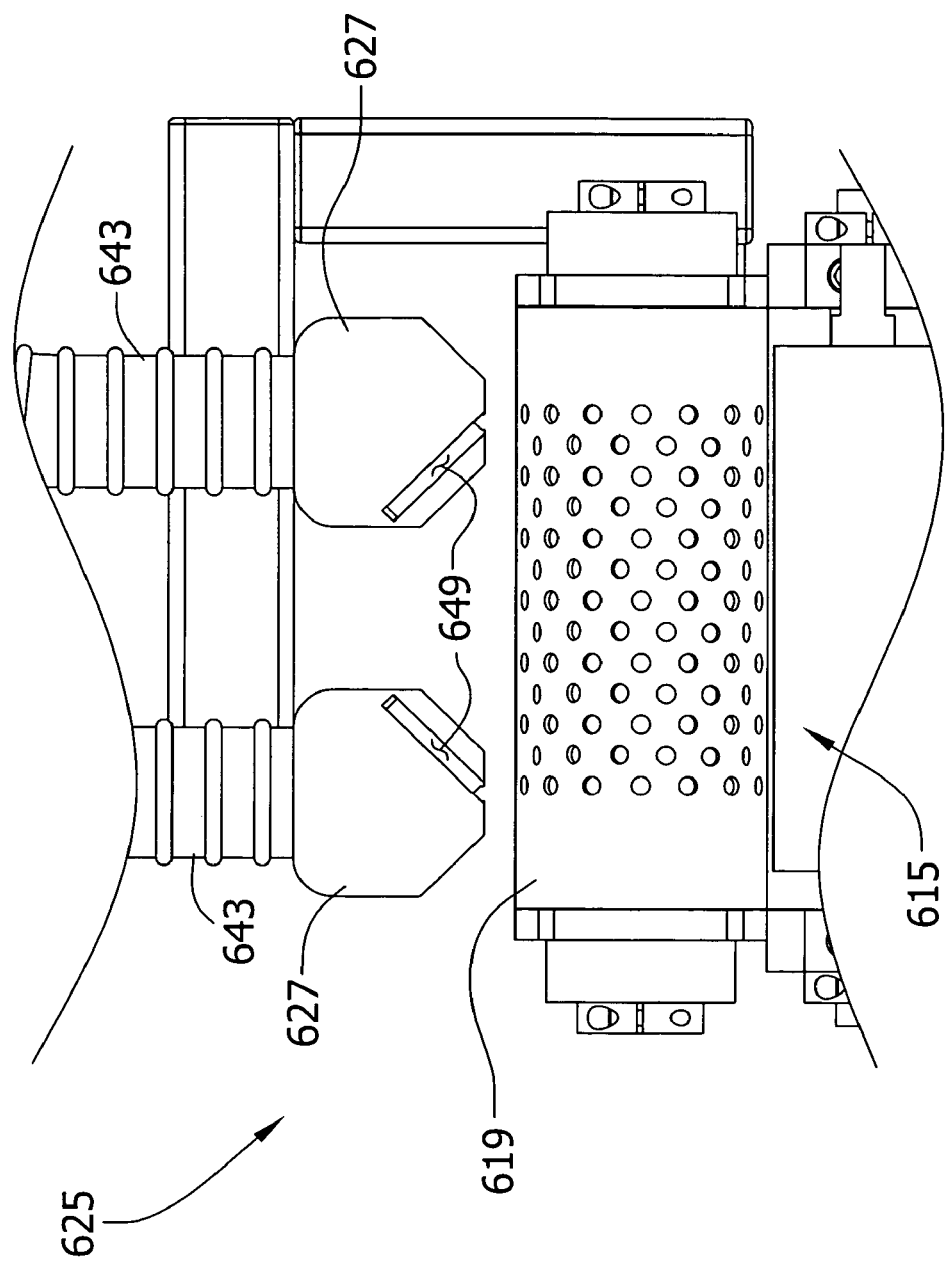
FIG. 32 is a partial rear elevation of the wrapping apparatus of FIG. 30.

The vacuum slot 649 suitably varies in angular orientation relative to the absorbent core web (e.g., relative to the foraminous belt 619) in a generally helical pattern as the vacuum slot extends longitudinally from the upstream to the downstream end of the vacuum unit 627. For example, the angular orientation of the vacuum slot relative to the foraminous belt 619 at the upstream end of the vacuum unit 627 as shown in FIG. 31 is approximately 135 degrees. The angular orientation of the vacuum slot 649 at a location generally midway along the length of the vacuum unit 627 is approximately 90 degrees as shown in FIG. 33. And the angular orientation of the vacuum slot 649 at the downstream end of the vacuum unit 627 as shown in FIG. 2 is approximately 45 degrees. It is understood, however, that the angular orientation of the vacuum slot 649 may be other than as described previously, as long as the vacuum slot varies in orientation from the upstream end to the downstream end of the vacuum unit and angular orientation of the vacuum unit at the downstream end thereof is nearer to the wrapped configuration of the wrapsheet web about the absorbent core and cover layer.

While not shown in the drawings, it is contemplated that the vacuum unit 627 of this fourth embodiment may have a guide member (e.g., similar in construction and arrangement to the guide member 263 of the first vacuum unit 227 of the embodiment of FIGS. 11-16) at the upstream end of the vacuum unit.

In operation, as the wrapsheet web, and overlying absorbent core web and cover layer web are conveyed by the conveying apparatus 615 to the wrapping apparatus 625, the wrapsheet web side margins (e.g., see FIG. 11 wherein the wrapsheet web portions extend laterally outward beyond the side edges of the absorbent core web) approach the upstream end of the vaccuum units 627. At the upstream end of each vacuum unit, air is drawn by the vacuum units 627 over both faces of the lateral side margins 119 (FIG. 11) of the wrapsheet web to draw the wrapsheet web side margins 119 up into the slots so that the side margins of the wrapsheet web become oriented in the angular orientation of the vacuum slots. Air is drawn into the vacuum slots 649 and flows over both faces of the wrapsheet web side margins to inhibit the side margins of the wrapsheet web against contact with vacuum units 627 within the vacuum slots. Pulling the wrapsheet web side margins taut in this manner reduces and inhibits wrinkles in the wrapsheet web and facilitates a tight wrapping of the wrapsheet web 203 about the absorbent core web 213.

As the webs exit the vacuum slots 649 at the downstream end of the vacuum units 627, suction from the vacuum box of the conveyor apparatus 615 draws the wrapsheet web side margins 119 down towards absorbent core web 213, against the cover layer web 214, e.g., similar to the arrangement shown in FIGS. 11 and 16. It is also contemplated that a ski (not shown) or other suitable urging member (not shown) may be disposed downstream of each vacuum unit 627, or of the combined set of vacuum units, and may even be attached to and extend downstream of one or both vacuum units 627, to urge the wrapsheet web side margins 119 down towards the absorbent core web 213, against the cover layer web 214, as the wrapsheet web 203 and absorbent core web are conveyed downstream of the wrapping apparatus.

The wrapping apparatus 625 shown in FIGS. 30-33 wraps the wrapsheet web about the absorbent core web with the webs in a bodyside-face down configuration. That is, the face of the absorbent core web that faces down against the foraminous belt 619 as the wrapsheet and core webs are moved past the wrapping apparatus 625 corresponds to what becomes the bodyside face 111 (FIG. 5) of the wrapped absorbent core 91 upon incorporation of the wrapped absorbent core into an absorbent article. It is contemplated, however, that the absorbent core web may be wrapped by the wrapsheet web with the bodyside-face up, e.g., whereby the wrapsheet web side margins 119 are wrapped down and around the side edges of the absorbent core web, without departing from the scope of this invention.

When introducing elements of the present invention or the preferred aspect(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or illustrated in the accompanying drawings shall be interpreted as illustrative and not in a limiting sense.

What is claimed is:

1. An absorbent structure for an absorbent article, the absorbent structure having longitudinal end regions and a central region extending longitudinally between and interconnecting the longitudinal end regions, said absorbent structure comprising:
   a non-woven absorbent core extending from one longitudinal end region of the absorbent structure through the central region thereof to the opposite longitudinal end region of said absorbent structure, the absorbent core having a first face, a second face opposite the first face, and laterally opposite side edges, said absorbent core having a first width at the central region of the absorbent structure and a second width at at least one of said longitudinal end regions of the absorbent structure, said second width being greater than said first width; and
   a liquid permeable wrapsheet wrapped about said first face, said laterally opposite side edges and at least a portion of said second face of the absorbent core to define a wrapped configuration of the wrapsheet, the wrapsheet having a substantially uniform width in its wrapped configuration whereby the wrapsheet is wrapped over the lateral side edges of the absorbent core at the at least one of said longitudinal end regions of the absorbent structure and is wrapped over upon itself free of any intervening absorbent core laterally outward of the lateral side edges of the absorbent core at said central region of the absorbent structure, said wrapsheet being constructed at least in part of a non-woven material and being secured in its wrapped configuration about the absorbent core at at least one securement region, said securement region having a length substantially less than the length of the absorbent structure.

2. The absorbent structure set forth in claim 1 wherein the wrapsheet is secured in its wrapped configuration about the absorbent core at at least two securement regions spaced laterally from each other, each securement region being disposed generally adjacent a respective side edge of the absorbent core and having a length substantially less than the length of the absorbent structure.

3. The absorbent structure set forth in claim 1 wherein the wrapsheet is secured in its wrapped configuration about the absorbent core at at least two discrete securement regions spaced longitudinally from each other, at least one securement region being disposed generally at one of said longitudinal end regions of the absorbent structure and at least one other securement region being disposed at the opposite longitudinal end region of the absorbent structure, each securement region having a length substantially less than the length of the absorbent structure.

4. The absorbent structure set forth in claim 3 wherein the wrapsheet is secured in its wrapped configuration about the absorbent core at at least four discrete securement regions, at least two of said securement regions being disposed at one of said longitudinal end regions of the absorbent structure and being spaced laterally from each other, and at least two other of said securement regions being disposed at the longitudinally opposite end region of the absorbent structure and spaced laterally from each other, each securement region having a length substantially less than the length of the absorbent structure.

5. The absorbent structure set forth in claim 4 wherein each of the securement regions is disposed adjacent a respective one of the lateral side edges of the absorbent core.

6. The absorbent structure set forth in claim 1 wherein the at least one securement region, is disposed at least in part in the central region of the absorbent structure.

7. The absorbent structure set forth in claim 6 wherein the wrapsheet is secured in its wrapped configuration about the absorbent core at at least two discrete securement regions spaced laterally from each other, each of said securement regions being disposed at least in part in the central region of the absorbent structure and having a length substantially less than the length of the absorbent structure.

8. The absorbent structure set forth in claim 7 wherein each of the securement regions is disposed adjacent a respective one of the lateral side edges of the absorbent core.

9. The absorbent structure set forth in claim 1 wherein the wrapsheet is secured in its wrapped configuration at at least one securement region disposed at said at least one longitudinal end region of the absorbent structure.

10. The absorbent structure set forth in claim 1 wherein the wrapsheet is secured in its wrapped configuration at laterally opposite securement regions disposed at the central region of the absorbent structure such that the wrapsheet is secured to itself free of any intervening absorbent core at said securement regions.

11. The absorbent structure set forth in claim 1 wherein the wrapsheet is secured in its wrapped configuration by autogenous bonding at said at least one securement region.

12. The absorbent structure set forth in claim 11 wherein the wrapsheet that wraps said at least a portion of the second face of the absorbent core is autogenously bonded to at least one the absorbent core and to a portion of the wrapsheet that wraps the first face of the absorbent core.

13. The absorbent structure set forth in claim 1 wherein the non-woven web is constructed at least in part of thermoplastic material.

14. The absorbent structure set forth in claim 13 wherein the wrapsheet comprises a layer of meltblown material laminated between two layers of spunbonded material.

15. The absorbent structure set forth in claim 1 wherein the wrapsheet comprises a layer of meltblown material laminated to the layer of spunbonded material.

16. An absorbent structure for an absorbent article, the absorbent structure having longitudinal end regions and a central region extending longitudinally between and interconnecting the longitudinal end regions, said absorbent structure comprising:

a non-woven absorbent core extending from one longitudinal end region of the absorbent structure through the central region thereof to the opposite longitudinal end region of said absorbent structure, the absorbent core having a first face, a second face opposite the first face, and laterally opposite side edges, and a width;

a cover layer covering the second face of the absorbent core across substantially the entire width of the absorbent core; and a liquid permeable wrapsheet wrapped about said first face, said laterally opposite side edges and at least a portion of the cover layer covering said second face of the absorbent core to define a wrapped configuration of the wrapsheet, said wrapsheet being constructed at least in part of a non-woven material and being secured in its wrapped configuration about the absorbent core at at least one securement region, said securement region having a length substantially less than the length of the absorbent structure.

17. The absorbent structure set forth in claim 16 wherein a portion of the wrapsheet is secured to the cover layer at said at least one securement region.

18. The absorbent structure set forth in claim 16 wherein the absorbent structure is free from absorbent core at said at least one securement region.

19. The absorbent structure set forth in claim 16 wherein a portion of the wrapsheet is secured to the cover layer and to at least one of the absorbent core and another portion of the wrapsheet at said at least one securement region.

20. An absorbent structure for an absorbent article, the absorbent structure having longitudinal end regions and a central region extending longitudinally between and interconnecting the longitudinal end regions, said absorbent structure comprising:

a non-woven absorbent core extending from one longitudinal end region of the absorbent structure through the central region thereof to the opposite longitudinal end region of said absorbent structure, the absorbent core having a first face, a second face opposite the first face, and laterally opposite side edges, said absorbent core having a width that varies as the core extends longitudinally from one longitudinal end of the absorbent structure to the opposite longitudinal end of said absorbent structure; and a liquid permeable wrapsheet wrapped in a wrapped configuration of the wrapsheet about said first face, a first longitudinally extending portion of said wrapsheet also being wrapped about the lateral side edges of the absorbent core and at least a portion of the second face of the absorbent core, a second longitudinally extending portion of said wrapsheet separate from said first portion of said wrapsheet also being wrapped over upon itself free of any intervening absorbent structure generally laterally outward of the lateral side edges of the absorbent core, said wrapsheet being constructed at least in part of a non-woven material and being secured in its wrapped configuration about the absorbent core at at least one securement region, said securement region having a length substantially less than the length of the absorbent structure.

21. An absorbent article for personal wear, said absorbent article comprising:

a bodyside liner;

an outer cover in opposed relationship with the bodyside liner; and an absorbent structure disposed between the bodyside liner and the outer cover and having longitudinal end regions and a central region extending longitudinally between and interconnecting the longitudinal end regions, said absorbent structure comprising a non-woven absorbent core extending from one longitudinal end region of the absorbent structure through the central region thereof to the opposite longitudinal end region of said absorbent structure, the absorbent core having a first face, a second face opposite the first face, and laterally opposite side edges, and a liquid permeable wrapsheet separate from the liner and the outer cover and wrapped about said first face, said laterally opposite side edges and at least a portion of said second face of the absorbent core to define a wrapped configuration of the wrapsheet, said wrapsheet being constructed at least in part of a non-woven material and being secured in its wrapped configuration about the absorbent core at at least one securement region, said securement region having a length substantially less than the length of the absorbent structure.

* * * * *